(12) United States Patent
Drake et al.

(10) Patent No.: US 11,524,143 B2
(45) Date of Patent: Dec. 13, 2022

(54) CATHETER WITH DISTAL AND PROXIMAL FIXATION MEMBERS

(71) Applicant: Medtronic, Inc., Minneapolis, MN (US)

(72) Inventors: Ronald A. Drake, St. Louis Park, MN (US); Lester O. Stener, Hudson, WI (US); Allan Roland Kilgore, Sarasota, FL (US); Paul Schadt, Shafer, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 16/918,192

(22) Filed: Jul. 1, 2020

(65) Prior Publication Data
US 2021/0016063 A1 Jan. 21, 2021

Related U.S. Application Data

(60) Provisional application No. 62/874,078, filed on Jul. 15, 2019.

(51) Int. Cl.
*A61M 25/01* (2006.01)
*A61M 25/09* (2006.01)

(52) U.S. Cl.
CPC ........ *A61M 25/0147* (2013.01); *A61M 25/09* (2013.01); *A61M 2025/015* (2013.01); *A61M 2025/09083* (2013.01)

(58) Field of Classification Search
CPC .......... A61M 25/0147; A61M 25/0068; A61M 25/0069; A61M 25/0133; A61M 25/0136;
(Continued)

(56) References Cited

U.S. PATENT DOCUMENTS 3,814,104 A 6/1974 Irnich et al.
3,943,936 A 3/1976 Rasor et al.
(Continued)

FOREIGN PATENT DOCUMENTS

EP 0254701 A1 1/1988
EP 1726326 A2 11/2006
(Continued)

OTHER PUBLICATIONS

Material Data Center | Datasheet Pebax® 7233 SA 01 MED (https://www.materialdatacenter.com/ms/en/Pebax/Arkema/Pebax®+7233+SA+01+MED/bdb26656/264), accessed Oct. 7, 2021 (Year: 2021).*

(Continued)

*Primary Examiner* — Emily L Schmidt
*Assistant Examiner* — Adam J. Cermak
(74) *Attorney, Agent, or Firm* — Shumaker & Sieffert, P.A.

(57) ABSTRACT

A deflectable catheter includes an elongate member having a wall defining a longitudinally extending lumen extending from a proximal end to a distal end, a fixation member coupled to an exterior surface of the wall on a distal portion of the elongate member, and a pull wire extending through the wall of the elongate member from the proximal end of the elongate member to the fixation member. The pull wire is coupled to the fixation member and constrained along its length such that the elongate member is configured to deflect from an initial configuration to a deflected configuration in response to a pull force applied to the pull wire and actively return from the deflected configuration to the initial configuration in response to a push force applied to the pull wire.

18 Claims, 17 Drawing Sheets

(58) Field of Classification Search
CPC ............ A61M 25/005; A61M 25/0053; A61M 2025/015; A61M 2025/09116; A61M 2025/0098; A61M 2025/0046–0048
See application file for complete search history.

(56) References Cited

U.S. PATENT DOCUMENTS

| | | | |
|---|---|---|---|
| 4,103,690 A | 8/1978 | Harris | |
| 4,142,530 A | 3/1979 | Wittkampf | |
| 4,233,734 A | 11/1980 | Bies | |
| 4,269,198 A | 5/1981 | Stokes | |
| 4,280,512 A | 7/1981 | Karr et al. | |
| 4,322,885 A | 4/1982 | Osada | |
| 4,858,623 A | 8/1989 | Bradshaw et al. | |
| 4,936,823 A | 6/1990 | Colvin | |
| 5,193,540 A | 3/1993 | Schulman et al. | |
| 5,318,526 A * | 6/1994 | Cohen | A61B 1/0055 604/95.04 |
| 5,411,535 A | 5/1995 | Fujii et al. | |
| 5,573,540 A | 11/1996 | Yoon | |
| 5,666,970 A | 9/1997 | Smith | |
| 5,683,447 A | 11/1997 | Bush et al. | |
| 5,702,373 A * | 12/1997 | Samson | A61M 25/005 604/526 |
| 6,007,558 A | 12/1999 | Ravenscroft et al. | |
| 6,030,360 A * | 2/2000 | Biggs | A61M 25/0136 600/139 |
| 6,146,338 A | 11/2000 | Gardeski et al. | |
| 6,146,355 A | 11/2000 | Biggs | |
| 6,151,525 A | 11/2000 | Soykan et al. | |
| 6,240,322 B1 | 5/2001 | Peterfeso et al. | |
| 6,286,512 B1 | 9/2001 | Loeb et al. | |
| 6,409,674 B1 | 6/2002 | Brockway et al. | |
| 6,571,131 B1 * | 5/2003 | Nguyen | A61B 18/1492 607/122 |
| 6,575,967 B1 | 6/2003 | Leveen et al. | |
| 6,599,296 B1 | 7/2003 | Gillick et al. | |
| 6,783,499 B2 | 8/2004 | Schwartz | |
| 6,915,149 B2 | 7/2005 | Ben-Haim | |
| 6,978,178 B2 | 12/2005 | Sommer et al. | |
| 7,290,743 B2 | 11/2007 | Nowack | |
| 7,418,298 B2 | 8/2008 | Shiroff et al. | |
| 7,419,477 B2 | 9/2008 | Simpson et al. | |
| 7,497,853 B2 * | 3/2009 | Fisher | A61M 25/0147 604/528 |
| 7,678,074 B2 | 3/2010 | Fischer et al. | |
| 7,993,384 B2 | 8/2011 | Wu et al. | |
| 8,177,773 B2 | 5/2012 | Ovcharchyn et al. | |
| 8,206,343 B2 | 6/2012 | Racz | |
| 8,353,940 B2 | 1/2013 | Benderev | |
| 8,676,290 B2 | 3/2014 | Tegg | |
| 8,706,260 B2 * | 4/2014 | Stewart | A61M 25/0147 607/122 |
| 8,721,587 B2 * | 5/2014 | Berthiaume | A61M 25/0147 604/95.04 |
| 8,784,468 B2 | 7/2014 | Gerdts et al. | |
| 8,790,386 B2 | 7/2014 | Dwork | |
| 8,911,487 B2 * | 12/2014 | Bennett | A61M 25/01 623/1.11 |
| 8,920,432 B2 | 12/2014 | Drake et al. | |
| 8,926,588 B2 | 1/2015 | Berthiaume et al. | |
| 9,414,857 B2 * | 8/2016 | Wood | A61N 1/362 |
| 9,526,522 B2 | 12/2016 | Wood et al. | |
| 9,592,364 B2 * | 3/2017 | Kaufmann | B23K 10/02 |
| 9,867,964 B2 * | 1/2018 | Drake | A61N 1/057 |
| 9,937,322 B2 * | 4/2018 | Drake | A61M 25/0097 |
| 2002/0103424 A1 | 8/2002 | Swoyer et al. | |
| 2002/0165589 A1 | 11/2002 | Imran et al. | |
| 2003/0088301 A1 | 5/2003 | King | |
| 2004/0059288 A1 | 3/2004 | Webler et al. | |
| 2004/0147973 A1 | 7/2004 | Hauser | |
| 2004/0230281 A1 | 11/2004 | Heil et al. | |
| 2005/0049574 A1 * | 3/2005 | Petrick | A61M 25/0026 604/525 |
| 2006/0084965 A1 | 4/2006 | Young | |
| 2006/0085039 A1 | 4/2006 | Hastings et al. | |
| 2006/0085041 A1 | 4/2006 | Hastings et al. | |
| 2006/0195117 A1 * | 8/2006 | Rucker | A61B 1/012 606/108 |
| 2008/0251966 A1 * | 10/2008 | Kampa | B29C 48/151 264/211.22 |
| 2009/0082828 A1 | 3/2009 | Ostroff | |
| 2010/0004633 A1 * | 1/2010 | Rothe | A61M 25/0082 604/528 |
| 2010/0059173 A1 * | 3/2010 | Kampa | A61M 25/0012 156/244.15 |
| 2010/0168827 A1 | 7/2010 | Schultz | |
| 2010/0274187 A1 * | 10/2010 | Argentine | A61M 25/0082 604/96.01 |
| 2012/0158021 A1 | 6/2012 | Morrill | |
| 2012/0172892 A1 | 7/2012 | Grubac et al. | |
| 2012/0271198 A1 * | 10/2012 | Whittaker | A61M 25/0158 600/585 |
| 2012/0277671 A1 * | 11/2012 | Fuentes | A61M 25/0147 604/95.04 |
| 2012/0323254 A1 | 12/2012 | Bonde et al. | |
| 2013/0079798 A1 | 3/2013 | Tran et al. | |
| 2013/0102960 A1 | 4/2013 | Miyoshi | |
| 2013/0103047 A1 | 4/2013 | Steingisser et al. | |
| 2013/0131667 A1 | 5/2013 | Jenson et al. | |
| 2013/0131693 A1 | 5/2013 | Berthiaume et al. | |
| 2014/0005647 A1 * | 1/2014 | Shuffler | A61M 25/0136 606/16 |
| 2014/0039591 A1 | 2/2014 | Drasler et al. | |
| 2014/0052109 A1 | 2/2014 | Organ et al. | |
| 2014/0074114 A1 | 3/2014 | Khairkhahan et al. | |
| 2014/0228800 A1 | 8/2014 | Rezac et al. | |
| 2014/0243844 A1 | 8/2014 | Clancy et al. | |
| 2014/0336456 A1 | 11/2014 | Demers et al. | |
| 2015/0039070 A1 | 2/2015 | Kuhn et al. | |
| 2015/0196736 A1 * | 7/2015 | Tegg | A61M 25/0136 604/95.04 |
| 2015/0246205 A1 | 9/2015 | Schaeffer | |
| 2016/0278851 A1 * | 9/2016 | Mannion | A61M 25/0147 |
| 2016/0310703 A1 | 10/2016 | Drake et al. | |
| 2017/0080186 A1 * | 3/2017 | Salahieh | A61B 1/0055 |
| 2017/0095662 A1 * | 4/2017 | McDonnell | A61N 1/37205 |
| 2017/0340863 A1 * | 11/2017 | Furnish | A61M 25/0133 |
| 2018/0071485 A1 * | 3/2018 | Gupta | A61M 25/01 |
| 2018/0126124 A1 * | 5/2018 | Winston | A61M 25/0052 |
| 2018/0178006 A1 * | 6/2018 | Soltis | A61N 1/3756 |
| 2018/0193605 A1 * | 7/2018 | Shumer | A61F 2/966 |
| 2018/0207402 A1 * | 7/2018 | Tegg | B29C 65/02 |
| 2018/0264231 A1 * | 9/2018 | Scheibe | A61M 25/0133 |
| 2018/0344981 A1 * | 12/2018 | Laduca | A61L 29/06 |
| 2021/0016056 A1 * | 1/2021 | Drake | A61M 25/005 |

FOREIGN PATENT DOCUMENTS

| | | | | |
|---|---|---|---|---|
| EP | 2465568 A1 | 6/2012 | | |
| EP | 2172241 B1 | 12/2012 | | |
| EP | 2204208 B1 | 12/2013 | | |
| EP | 2764886 B1 | 9/2016 | | |
| EP | 3695871 A1 * | 8/2020 | | A61M 25/0147 |
| JP | 04073069 A * | 3/1992 | | A61M 25/09 |
| JP | 2012139345 A | 7/2012 | | |
| WO | 2002022202 A2 | 3/2002 | | |
| WO | 2006118865 A2 | 11/2006 | | |
| WO | WO-2012061657 A2 * | 5/2012 | | A61M 25/0136 |
| WO | 2012096816 A1 | 7/2012 | | |
| WO | WO-2012096816 A1 * | 7/2012 | | A61M 25/10 |
| WO | WO-2014203336 A1 * | 12/2014 | | A61M 25/005 |
| WO | WO-2020053233 A1 * | 3/2020 | | A61B 34/70 |

OTHER PUBLICATIONS

Material Data Center | Datasheet Pebax® 3533 SA 01 MED (https://www.materialdatacenter.com/ms/en/Pebax/Arkema/Pebax®+3533+SA+01+MED/f735364d/264), accessed Oct. 7, 2021 (Year: 2021).*

(56) References Cited

OTHER PUBLICATIONS

U.S. Appl. No. 16/915,118, naming Inventors: Drake et al., filed Jun. 29, 2020.
International Search Report and Written Opinion of International Application No. PCT/US2020/041929, dated Nov. 6, 2020, 9 pp.
Haqqani et al., "The Implantable Cardioverter-Defibrillator Lead: Principles, Progress and Promises," PACE, vol. 32, Oct. 2009, pp. 1336-1353.
Tjong et al., "Acute and 3-Month Performance of a Communicating Leadless Antitachycardia Pacemaker and Subcutaneous Implantable Defibrillator," JACC: Clinical Electrophysiology, vol. 3, No. 13, Dec. 26, 2017, pp. 1487-1498.
Tjong et al., "The modular cardiac rhythm management system: the EMPOWER leadless pacemaker and the EMBLEM subcutaneous ICD," Herzschrittmachertherapie + Elektrophysiologie, vol. 29, Oct. 31, 2018, pp. 355-361.
Office Action from U.S. Appl. No. 16/915,118, dated Apr. 27, 2022, 34 pp.
Response to Office Action dated Apr. 27, 2022 from U.S. Appl. No. 16/915,118, filed Jul. 27, 2022, 30 pp.
Notice of Allowance from U.S. Appl. No. 16/915,118 dated Aug. 19, 2022, 9 pp.

\* cited by examiner

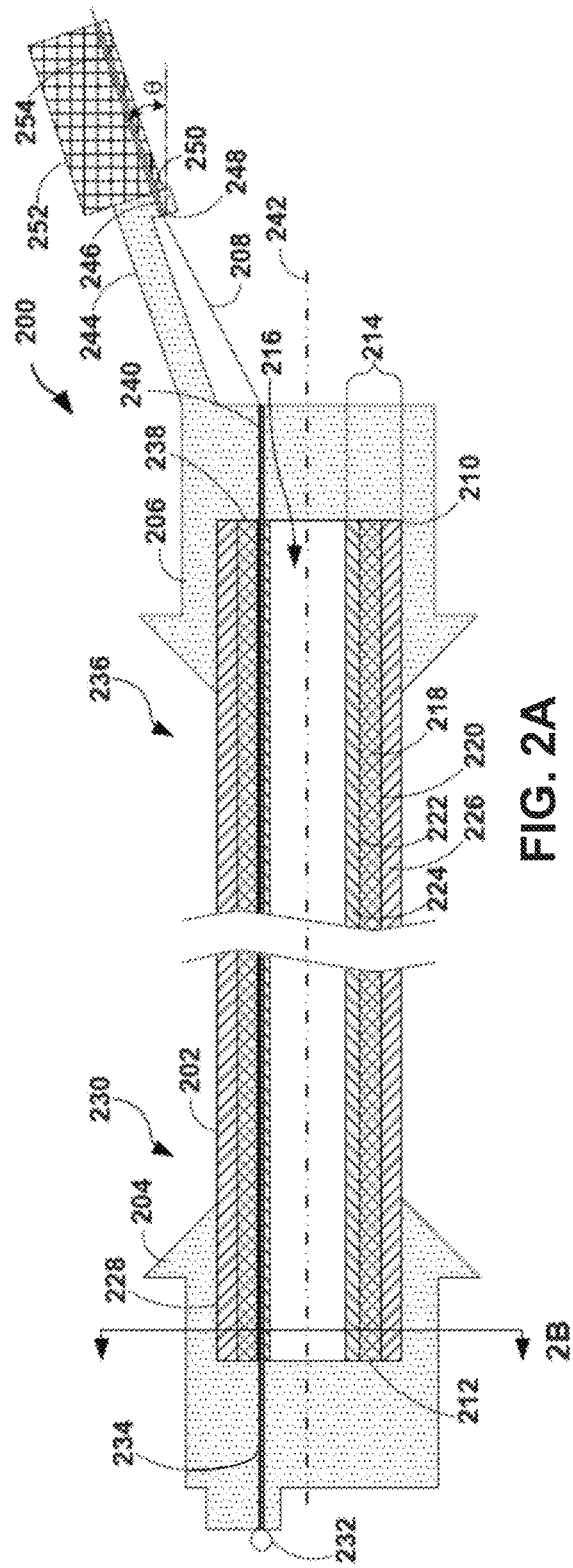
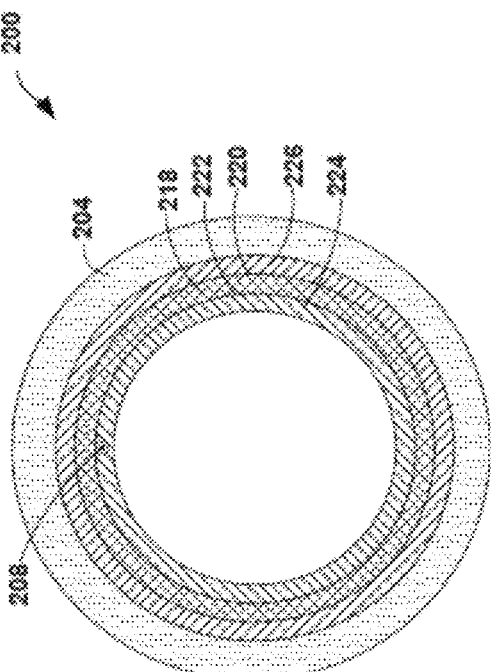
FIG. 2A
FIG. 2B

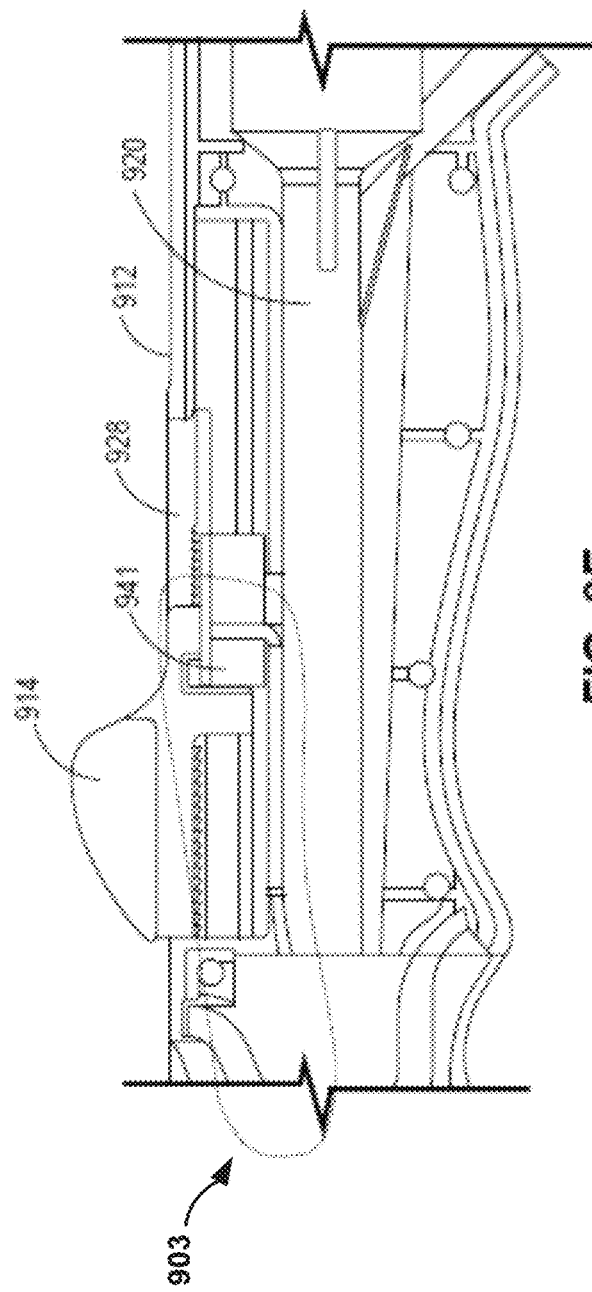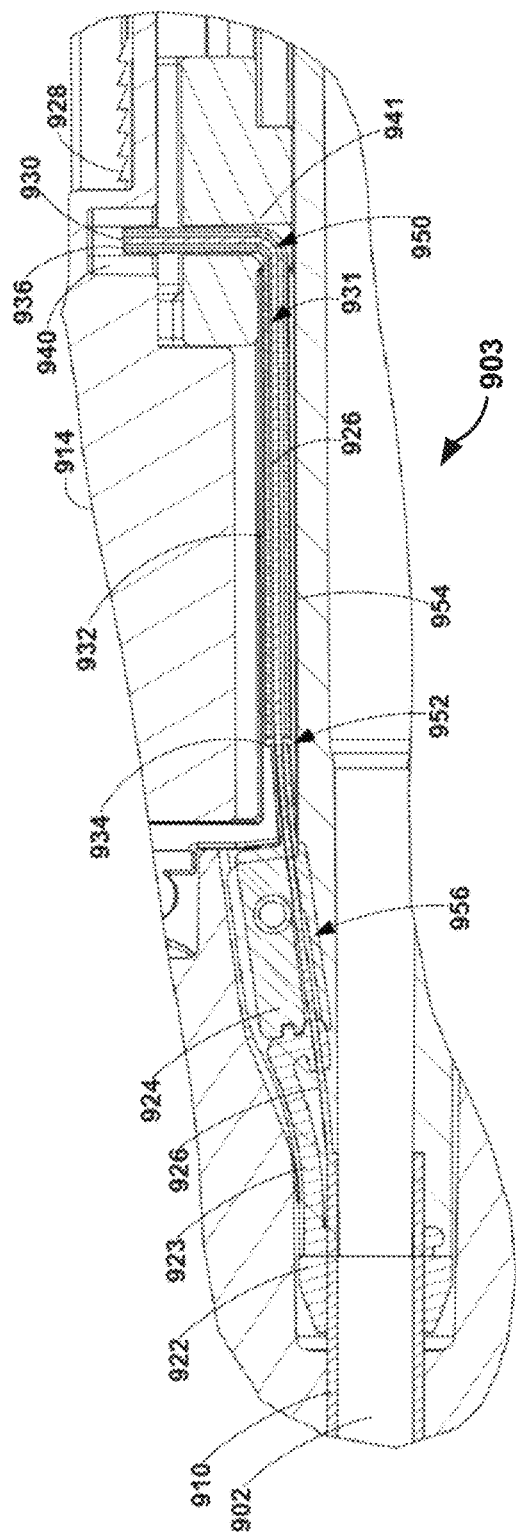
FIG. 9E
FIG. 9F

CATHETER WITH DISTAL AND PROXIMAL FIXATION MEMBERS

This application claims the benefit of U.S. Provisional Application Ser. No. 62/874,078, entitled "CATHETER WITH DISTAL AND PROXIMAL FIXATION MEMBERS," and filed on Jul. 15, 2019, the entire content of which is incorporated herein by reference.

TECHNICAL FIELD

This disclosure relates to medical systems and techniques including deflectable shaft catheters.

BACKGROUND

Interventional medicine techniques may use deflectable shaft catheters to deliver medical therapy and/or provide medical monitoring. Typically, a deflectable shaft catheter includes a pull wire extending along a length thereof, where a distal end of the pull wire is anchored to a pull band on the shaft at a location just distal to a deflectable segment of the shaft. A proximal end of the pull wire is typically secured to a control member subassembly mounted in a handle of the catheter.

SUMMARY

The present disclosure describes example medical systems including deflectable catheters and techniques including the use and manufacture of deflectable catheters. The described deflectable catheters include a pull wire that may have an overmolded distal end, an overmolded proximal end, or both. Components of the overmolded distal and/or proximal end may provide a channel for the pull wire that is substantially leak-free and enables a push force to be applied to the pull wire (e.g., by a control member). For example, when grasping the catheter handle, a clinician may actuate the pull wire by applying a force to the control member, thereby deflecting the catheter shaft from an initial (e.g., substantially straight) configuration to a deflected (e.g., curved or otherwise bent) configuration. The deflected configuration may enable a clinician to maneuver a distal portion of the shaft toward a target site within a body of a patient. Upon releasing the control member, or actively returning the control member to a home position, the pull wire may actively apply a push force from the control member to the distal end of the catheter shaft to return the catheter shaft to the initial configuration.

In some examples, a catheter may include an elongate member, a fixation member, and a pull wire. The elongate member may extend from a proximal end to a distal end, where the elongate member includes a wall defining a longitudinally extending lumen. The fixation member may be coupled to an exterior surface of the wall on a distal portion of the elongate member. The pull wire may extend through the wall of the elongate member from the proximal end of the elongate member to the fixation member. The pull wire may be coupled to the fixation member. The elongate member may be configured to deflect from an initial configuration to a deflected configuration in response to a pull force applied to the pull wire.

In some examples, a catheter may include an elongate member extending from a proximal end to a distal end, the elongate member including a wall defining a longitudinally extending lumen; a distal fixation member coupled to an exterior surface of the wall on a distal portion of the elongate member; a proximal fixation member coupled to an exterior surface of the wall on a proximal portion of the elongate member; a retention arm integrally formed with the proximal fixation member, where the retention arm may be configured to retain the pull wire in sliding engagement at an angle extending away from a longitudinal axis of the elongate member; a pull wire extending from a distal end coupled to the distal fixation member, through the wall of the elongate member, to a distal portion extending through the proximal fixation member and retention arm, and wherein the elongate member is configured to deflect from an initial configuration to a deflected configuration in response to a pull force applied to the pull wire.

In some examples, a method may include forming an elongate member extending from a proximal end to a distal end, the elongate member including a wall defining a longitudinally extending lumen. The method also may include overmolding a fixation member onto an exterior surface of the wall on a distal portion of the elongate member. The method also may include anchoring a pull wire to the fixation member, the pull wire extending through the wall of the elongate member from the proximal end of the elongate member to the fixation member, and the elongate member configured to deflect from an initial configuration to a deflected configuration in response to a pull force applied to the pull wire.

The details of one or more examples are set forth in the accompanying drawings and the description below. Other features, objects, and advantages will be apparent from the description and drawings, and from the claims.

BRIEF DESCRIPTION OF THE DRAWINGS

FIGS. 2A-2C are conceptual diagrams illustrating lateral and axial cross-sectional views of an example catheter.

FIGS. 9A-9F are conceptual diagrams illustrating an example handle of a deflection assembly of a catheter.

DETAILED DESCRIPTION

The disclosure describes example medical systems including deflectable catheters and techniques including the use and manufacture of deflectable catheters. An example deflectable catheter includes an elongate member and a deflection assembly. The deflection assembly includes a handle, an elongate pull wire, and a control member. The elongate member includes a wall extending from a proximal end to a distal end and defining a longitudinally extending lumen. The proximal end of the elongate member may be coupled to a handle of the deflection assembly. The elongate pull wire of the deflection assembly extends from a fixation member at a distal portion of the elongate member to the control member, e.g., through at least a portion of the wall of the elongate member.

When a clinician slides the control member proximally the distal portion of the elongate member may deflect from an initial configuration to a deflected configuration. When the clinician releases the control member or pushes the control member back distally to the home position, the pull wire actively pushes the elongate member back to the initial configuration. For example, a perimeter of the pull wire may be constrained from the fixation member at the distal portion of the elongate member to the control member. By constraining the pull wire, a push force applied to the pull wire may be translated from the control member to the distal portion of the elongate member, rather than, an unconstrained pull wire bending or buckling in response to a push force. Translation of the push force by the constrained pull wire enables active return of the elongate member from a deflected configuration to its initial configuration, which may be a substantially straight configuration.

By enabling active return using a single pull wire, the described deflectable catheters provide enhanced function compared to deflectable catheters without active return. For example, a deflectable catheter without active return, upon release of a control member of when in a deflected configuration, may relax toward the initial configuration due to release of strain in the elongate member. In some examples, the return to initial configuration may be due to elastic deformation of at least a portion of the elongate member. In some examples, the deflectable catheter without active return may be unable to fully return to the initial configuration, for example, due to plastic deformation of at least a portion of the elongate member. An active return deflectable catheter, however, may be controlled to return to the initial configuration. In some examples, an active return deflectable catheter may extend beyond the initial configuration, e.g., deflect in a second direction opposite the deflected configuration.

Figure 1:
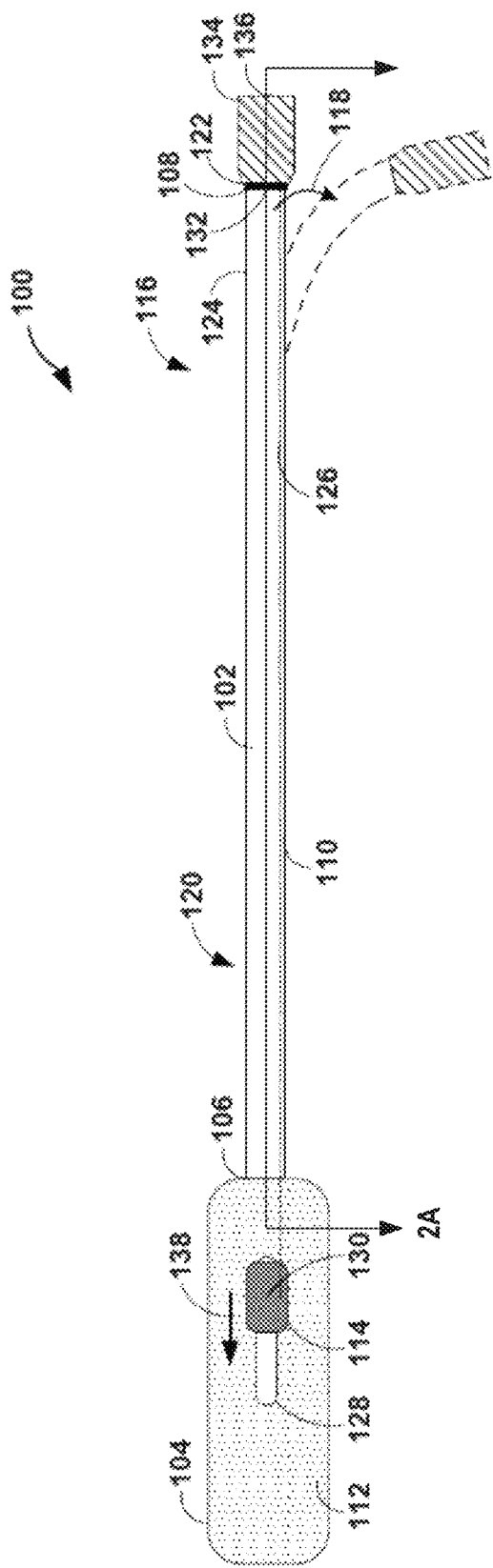
FIG. 1 is a schematic and conceptual diagram illustrating a plan view of an example deflectable catheter.

FIG. 1 is a schematic and conceptual diagram illustrating a plan view of an example deflectable catheter 100. Deflectable catheter 100 includes an elongate member 102 and a deflection assembly 104. Elongate member 102 extends from a proximal end 106 to a distal end 108. Elongate member 102 includes a wall 110 defining a longitudinally extending lumen (not shown).

Wall 110 may include one or more material layers. For example, wall 110 may include one or more polymeric material layers. In some examples, wall 110 may include an elongate core layer, an inner layer, and an outer layer. The elongate core layer may include a substantially resilient material, e.g., relative to the inner layer and/or outer layer.

In some examples, elongate core layer may include a coiled or braided metal wire, such as, for example, stainless steel or nitinol, defining an exterior surface and an interior surface defining the lumen of elongate member 102. The inner layer may include a polymer, such as, for example, polytetrafluoroethylene or other polymer having a low coefficient of friction (e.g., relative to the elongate core layer), disposed on the interior surface of the elongate core layer. The outer layer may include a polymer, such as, for example, polyether block amide or other flexible polymers, disposed on the exterior surface of the elongate core layer.

Proximal portion (e.g., proximal end 106) of elongate member 102 is coupled to deflection assembly 104. Deflection assembly 104 includes a hub assembly (not shown), a handle 112, a control member 114, and a pull wire 126. The hub assembly may be coupled to at least a portion of proximal portion 120 (e.g., proximal end 106) of elongate member 102. For example, the hub assembly may be overmolded onto the portion of proximal portion 120 of elongate member 102. Handle 112 may be configured to surround and engage at least a portion of the hub assembly. Additionally, or alternatively, at least a portion of proximal portion 120 (e.g., proximal end 106) of elongate member 102 may be coupled directly to handle 112. Control member 114 may be slidably engaged with handle 112. For example, handle 112 may define track 128, along which control member 114 may move (e.g., in the proximal-distal direction).

Pull wire 126 extends from a proximal end 130 to a distal end 132. Proximal end 130 of pull wire 126 may be coupled to control member 114. In some examples, deflection assembly 104 may include a hypotube (not shown) extending from a distal end of the hypotube directly coupled to proximal end 130 of pull wire 126 to a proximal end of the hypotube directly coupled to control member 114. Pull wire 126 may extend through, for example, at least a portion of the hub assembly, handle 112, and/or wall 110 of elongate member 102. For example, handle 112 may include a handle surround (not shown) configured to surround at least a portion of pull wire 126 and/or the hypotube extending from the hub assembly to control member 114. Pull wire 126 may include any suitable inextensible and/or incompressible material. In some examples, pull wire 126 may include a metal, such as, stainless steel or nitinol, formed into an elongate wire, coil, or braid.

Distal end 132 of pull wire 126 may be coupled (e.g., anchored) to a fixation member 122. Fixation member 122 may be coupled to an exterior surface 124 of wall 110 on distal portion 116 of elongate member 102. For example, fixation member 122 may include one or more components configured to mechanically couple pull wire 126 to distal portion 116 of elongate member 102. In some examples, fixation member 122 may include a ferrule, a collet, a compression fitting, or any suitable annular fitting overmolded or mechanically coupled (e.g., adhered or friction fit) to exterior surface 124 of wall 110 of elongate member 102. In this way, fixation member 122 may be configured to engage exterior surface 124 of wall 110 of elongate member 102. In some examples, fixation member 122 also may include a channel or a protrusion configured to receive distal portion 132 of pull wire 126. In some examples, distal end 132 of pull wire 126 may include an anchor, such as a bulbous structure (e.g., having a diameter larger than a diameter of pull wire 126), a washer, a loop, or a knot, to enable fixation member 122 to securely retain distal portion 132 of pull wire 126.

In some examples, distal portion 116 (e.g., distal end 108) of catheter 100 may include a distal cup 134. Distal cup 134 may extend from fixation member 122 to distal tip 136. Distal cup 134 may be configured to encase at least a portion of fixation member 122. For example, distal cup 134 may be overmolded onto at least a portion of fixation member 122 and/or distal end 132 of elongate pull wire 126. In some examples, distal cup 134 may include any suitable material, such as one or more polymers. At least one of a tensile strength of the one or more polymers of distal cup 134 may be greater than a tensile strength of a material of elongate member 102 or a durometer of the one or more polymers of distal cup 134 may be greater than a durometer of the material of elongate member 102. In this way, distal cup 134 may include a polymer material that is tougher than an outer layer of elongate member 102. The relative toughness of distal cup 134 may improve the robustness of pulling and pushing on pull wire 126, for example, compared to an attachment of a pull wire directly to elongate member 126 or an anchor band embedded in elongate member 126.

In some examples, distal cup 134 may be configured to receive an implantable medical device (IMD). For example, distal cup 134 may be configured to receive an implantable electrical therapy device, such as a cardiac pacing device. In some examples, distal cup 134 may be configured to deploy the 1 MB. For example, a clinician may introduce distal portion 116 of elongate member 202 into vasculature of a patient. The clinician may guide distal cup 134 to a target site within the vasculature of a patient. The target site may include, for example, a target pacing site. Once positioned at the target site, the clinician may deploy the 1 MB from distal tip 136 of distal cup 134. For example, deflectable catheter 100 may include any suitable deployment member configured to deploy the IMD from distal tip 136 of distal cup 134. In some examples, the deployment member may include a control wire having a proximal end coupled to a control member at deflection assembly 104, a medial portion extending through elongate member 102, and a distal end configured to push IMD out of distal cup 134.

At least a portion of a distal portion 116 of elongate member 102 is configured to deflect, e.g., in the direction of arrow 118, from an initial configuration (e.g., shown as solid lines in FIG. 1) to a deflected configuration (e.g., shown as dashed lines in FIG. 1). Proximal portion 120 of elongate member 102 may be configured to not deflect when distal portion 116 is deflected. When a clinician slides control member 114 proximally, as indicated by arrow 138, the distal portion of elongate member 102 may deflect from the initial configuration to the deflected configuration. In some examples, the initial configuration may include a substantially straight configuration, e.g., a straight or nearly straight configuration of elongate member 102. In some examples, the initial configuration may include a bent configuration, e.g., elongate member 102 may define a curve or bend when in a relaxed state without application of a pull force or push force. In some examples, the deflected configuration may include any suitable deflection relative to the initial configuration.

In some examples, the deflection occurs on the distal portion of elongate member 102 because wall 110 of elongate member 102 is more flexible or more compressible along distal portion 116 relative to proximal portion 120. Generally, the deflected configuration may include any suitable arc degree and/or radius of curvature. In some examples, the arc degree of the deflected configuration may be within a range from about 10 degrees to about 180 degrees, such as from about 20 degree to about 90 degrees. In some examples, the deflected configuration may include two or more deflections in the same direction or different directions. The first and second deflections may be at the same or different longitudinal position relative to elongate member 102. For example, the deflected configuration may include a first deflection (e.g., in the plane of the page as illustrated in FIG. 1) and a second deflection in a second direction at the same or a different longitudinal position (e.g., out of the plane of the page as illustrated in FIG. 1).

When the clinician releases control member 114 or pushes the control member back distally to a home position, pull wire 126 actively pushes elongate member 102 back to the initial configuration. For example, a perimeter of pull wire 126 may be constrained (e.g., surrounded) from fixation member 122 at distal end 108 of elongate member 102 to control member 114. By constraining pull wire 126, a push force applied to pull wire 126 may be transferred from control member 114 to distal portion 116 of elongate member 102, rather than, an unconstrained pull wire bending or buckling in response to the push force. Transfer of the push force by the constrained pull wire 126 enables active return of elongate member 102 from the deflected configuration to the initial configuration. By enabling active return using a single pull wire, the described deflectable catheters provide enhanced function compared to deflectable catheters without active return. For example, a deflectable catheter without active return, upon release of a control member when in a deflected configuration, may relax toward the initial configuration due to release of strain or elastic deformation in the elongate member. In some examples, a deflectable catheter without active return may be unable to fully return to an initial configuration, for example, due to plastic deformation of at least a portion of the elongate member. Active return deflectable catheter 100, however, may be controlled to return to the initial configuration, as described above.

In some examples, an active return deflectable catheter may extend beyond the initial configuration, e.g., deflect in a second direction opposite the deflected configuration. In some examples, deflection assembly 104 may include a dampening member configured to dampen a force applied to control member 114 in a distal direction, a proximal direction, or both. In this way, a clinician may move the control member back distally to the home position while the elongate member actively returns at a slightly dampened rate to the initial configuration. In some examples, the dampening member may include a spring positioned within the handle and mechanically coupled to the control member such that when the control member is pulled proximally the spring is not engaged (under compression or tension), but when the control member is pushed distally the spring is engaged under compression (e.g. to act as a shock absorber). In some examples, the spring also may provide for some active straightening.

FIGS. 2A and 2B are conceptual diagrams illustrating lateral and axial cross-sectional views of an example catheter 200. Catheter 200 may be the same as or substantially similar to deflectable catheter 100 describe above in reference to FIG. 1, except for the differences described herein. Catheter 200 includes elongate member 202, distal fixation member 204, proximal fixation member 206, and pull wire 208. Distal fixation member 204 and proximal fixation member 206 are configured to enable overmolding of a cup at the distal end of catheter 200 and a hub at the proximal end of catheter 200. For example, without distal fixation member 204 and proximal fixation member 206 overmolding the cup and the hub onto catheter 200 may compress or deform catheter 200. In some examples, distal fixation member 204 and proximal fixation member 206 may be overmolded onto catheter 200 using less pressure relative to a high pressure overmolding of the cup and the hub. In some examples, proximal fixation member 206 may include a ferrule that enables overmolding pull wire 208 (or sacrificial wire), such that the wire can extend out of the overmolding mold without the overmold material being expelled from the mold.

Elongate member 202 extends from proximal end 210 to distal end 212. As discussed above, elongate member 202 may be configured to deflect from an initial configuration to a deflected configuration in response to a pull force applied to pull wire 208 (e.g., in the proximal direction) and actively return from the deflected configuration to the initial configuration in response to a push force applied to pull wire 208 (e.g., in the distal direction). Elongate member includes wall 214 defining a longitudinally extending lumen 216. Wall 214 may include an elongate core layer 218, inner layer 224, and exterior layer 226, as discussed above. Elongate core layer 218 defines an exterior surface 220 and an interior surface 222. Interior surface 222 may define longitudinally extending lumen 216. Inner layer 224 may be disposed on interior surface 222 of elongate core layer 218. Outer layer 226 may be disposed on exterior surface 220 of elongate core layer 218. In some examples, pull wire 208 may extend through inner layer 224 from proximal end 210 to distal end 212 of elongate member 202. In some examples, pull wire 208 may extend through a separate dedicated lumen between inner layer 224 and core layer 218. In some examples, pull wire 208 may extend through both proximal fixation member 206 and distal fixation member 204.

Distal fixation member 204 is coupled to an exterior surface 228 of wall 214 on a distal portion 230 of elongate member 202. Distal fixation member 204 may include at least one of a ferrule or a collet configured to engage exterior surface 228 by at least one of a friction fit, a compression fit, or another mechanical fitting, such as by adhesion or overmolding. Distal fixation member 204 is configured to couple to distal end 232 of pull wire 208. For example, distal fixation member 204 may define a distal fixation channel 234 through which pull wire 208 may extend in sliding engagement. In some examples, distal end 232 of pull wire 208 may defined or include a bulbous structure (e.g., a structure having a diameter larger than a diameter of pull wire 208), a washer, a loop, or a knot. In this way, when a pull force is applied to pull wire 208 (e.g., in the proximal direction), distal end 232 may transfer the pull force to distal fixation member 204 and elongate member 202. In some examples, a distal cup (e.g., distal cup 134) may be coupled to distal fixation member 204 and distal end 232 of pull wire 208. The distal cup may be configured to, when a push force is applied to pull wire 208 (e.g., in the distal direction), transfer the push force from distal end 232 to the distal cup, distal fixation member 204, and elongate member 202. In this way, the distal end of catheter 200 is configured to transfer both a push force and pull force via a single pull wire 208 for deflection and active return of elongate member 202.

Proximal fixation member 206 is coupled to exterior surface 228 of wall 214 of elongate member 202 on a proximal portion 236 (e.g., proximal end 238) of elongate member 202. Proximal fixation member 206 may include at least one of a ferrule or a collet configured to engage exterior surface 228 of wall 214 of elongate member 202 by at least one of a friction fit, a compression fit, or another mechanical fitting, such as by adhesion or overmolding. Proximal fixation member 206 may be configured to retain pull wire 208 in sliding engagement. For example, proximal fixation member 206 may define a proximal retention channel 240 configured to retain pull wire 208 in sliding engagement. In some examples, proximal fixation member 206 may be configured to deflect pull wire 208 away from longitudinal axis 242, e.g., along which elongate member 202 extends. For example, proximal fixation member 206 may include a retention arm 244 extending from proximal fixation member 206 (e.g., the ferrule or the collet of proximal fixation member 206). Retention arm 244 may be integrally formed with proximal fixation member 206 or fixed to proximal fixation member 206 by, for example, an adhesive. Retention arm 244 may include a retention channel 246 extending from a distal end 248 to a proximal end 250 thereof at an angle θ relative to longitudinal axis 242 of elongate member 202. In some examples, proximal end 250 may define a ferrule. Retention channel 246 may be configured to retain pull wire 208 in sliding engagement. In this way, proximal fixation member 206 may orient pull wire 208 away from elongate member 202 such that a proximal end of pull wire 208 may be coupled to a control member of a deflection assembly (e.g., control member 114 of deflection assembly 104).

In some examples, proximal fixation member 206 also may include a reveal surround 252. In some examples, the reveal 252 is not attached to proximal end 250. For example, proximal end 250 may include a ferrule, such that both proximal end ferrule 250 and reveal 252 may be placed in a mold for overmolding. As a hub is overmolded onto proximal fixation member 206, reveal 252 may allow proximal end ferrule 250 to seal (e.g., such that the overmold material is not expelled from the mold) while pull wire 208 (or sacrificial wire) can extend through an aperture of the mold. After the overmolded proximal fixation member 206 cools, the sacrificial wire may be pulled out leaving retention channel 246. The final pull wire 208, in some examples having a smaller diameter than the sacrificial wire, may be inserted through the distal end of catheter 200 and out reveal 252. Alternately, the reveal surround 252 may couple to retention arm 244, for example, by a mechanical interlock or an adhesive. Reveal surround 252 may include a reveal surround channel 254. Reveal surround channel 254 may extend from a distal end to a proximal end thereof at angle θ relative to longitudinal axis 242 of elongate member 202. In other examples, reveal surround channel 254 may extend at an angle different than that of retention arm channel 246. Reveal surround 252 may be configured to retain pull wire 208 in sliding engagement. Reveal surround may enable a hub assembly to be overmolded onto catheter 100 such that pull wire 208 is fluidically isolated from lumen 216. In this way, catheter 200 may include a leak resistant or leak proof pull wire assembly.

Distal fixation member 204 and proximal fixation member 206 may include any suitable material. In some examples, distal fixation member 204 and/or proximal fixation member 206 may include a heat moldable polymer. For example, distal fixation member 204 and/or proximal fixation member 206 may be overmolded onto a respective distal portion 230 or proximal portion 236 of elongate member 202. In some examples, distal fixation member 204 and/or proximal fixation member 206 may be overmolded around pull wire 208 or around a sacrificial wire that may be replaced with pull wire 208 after overmolding proximal fixation member 206.

Figure 2C:
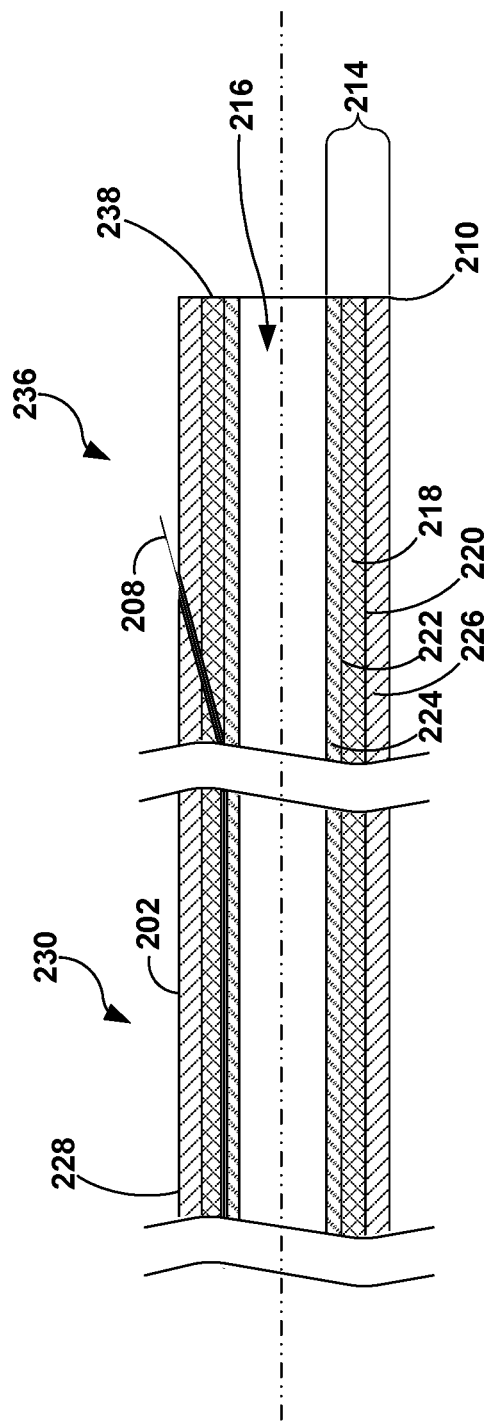

Pull wire 208 may be the same as or substantially similar to pull wire 126 discussed above in reference to FIG. 1. For example, pull wire 208 extends through wall 214 of elongate member 202 from proximal end 238 of elongate member 202 to distal fixation member 204, and pull wire 208 may be coupled to distal fixation member 204. Pull wire 208 may extend through inner layer 224 or be disposed between inner layer 224 and core layer 218. In some examples, as illustrated in FIG. 2C, pull wire 208 may protrude through outer layer 226 at proximal end 238 of elongate member 202. In other examples, as illustrated in FIG. 2C, pull wire 208 may protrude through core layer 218 and outer layer 226 to exterior surface 228 of wall 214 at proximal portion 236 of elongate member 202 (e.g., at a location distal to proximal end 238 of elongate member 202). In some examples, pull wire 208 may include a sheath or tube surrounding at least a portion of pull wire 208.

Figure 3A:
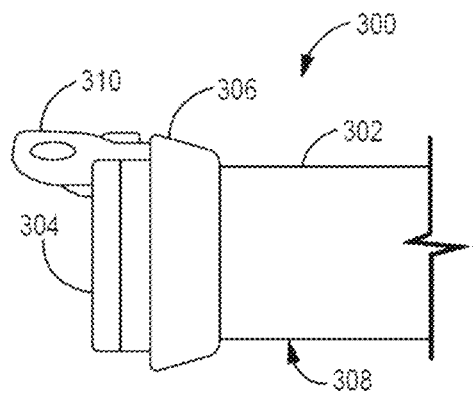
FIGS. 3A and 3B are conceptual diagrams illustrating an example distal fixation member on a distal end of an elongate member of an example catheter.
Figure 3B:
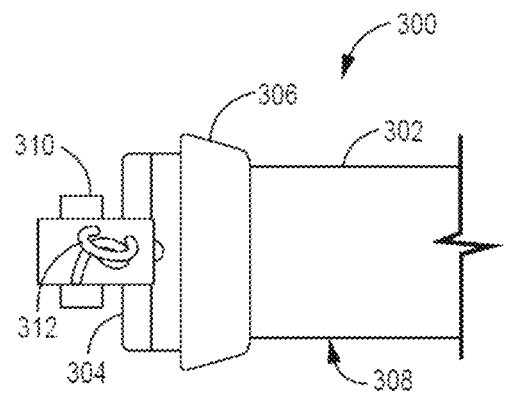

FIGS. 3A and 3B are conceptual diagrams illustrating an example distal fixation member 306 on a distal end 304 of an elongate member 302 of an example catheter 300. Catheter 300 may be the same as or substantially similar to catheters 100 and 200 discussed above in reference to FIGS. 1-2B. Distal fixation member 306 is coupled to distal portion 308 of elongate body 302, as discussed above. Distal fixation member 306 includes a fixation arm 310 to which pull wire 312 may be coupled. For example, pull wire 312 includes two loops surrounding a portion of fixation arm 310. In some examples, at least a distal portion of pull wire 312 may be encased in fixation arm 310, e.g., distal fixation member 306 may be overmolded over at least a distal portion of pull wire 312. By surrounding the portion of fixation arm 310, pull wire 312 may transfer a pull force and/or a push force to fixation member 306 and elongate member 302, as discussed above in reference to FIGS. 1-2B.

Figure 4:
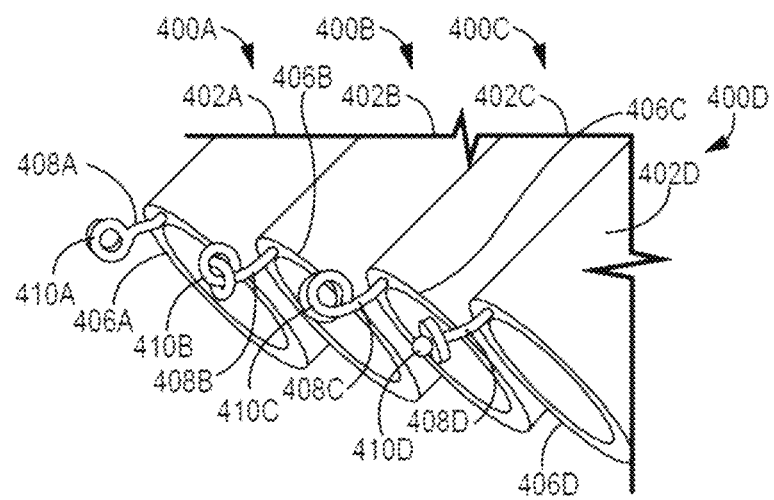
FIG. 4 is a conceptual and schematic diagram illustrating different configurations of distal ends of pull wires of respective example catheters.

FIG. 4 is a conceptual and schematic diagram illustrating different configurations of distal ends 410A, 410B, 410C, and 410D of respective pull wires 408A, 408B, 408C, and 408D protruding from respective distal ends 406A, 406B, 406C, and 406D of respective walls of respective elongate members 402A, 402B, 402C, and 402D of respective catheters 400A, 400B, 400C, and 400D (collectively, "catheters 400"). Catheters 400 may be the same as or substantially similar to any one or more of catheters 100, 200, and 300 discussed above in reference to FIGS. 1-3B. As illustrated in FIG. 4, distal end 410A includes a double loop having a centroid substantially aligned with an axis of pull wire 408A. Distal end 410B includes an overhand knot. In other example, distal end may include other types of knots. Distal end 410C includes a double loop having a centroid displaced from an axis of pull wire 408C. Distal end 410D includes bulbous structure, such as a bead of metal weld, and a washer. Any of the distal ends 410 of pull wires 408 may also contain a weld or adhesive to enhance strength. As discussed above, distal ends 410A, 410B, 410C, and 410D are configured to engage a fixation member and/or a distal cup (e.g., a portion of an overmolded distal cup) to enable respective pull wires 408A, 408B, 408C, and 408D to transfer a push force and/or a pull force to respective elongate members 402A, 402B, 402C, and 402D.

Figure 5A:
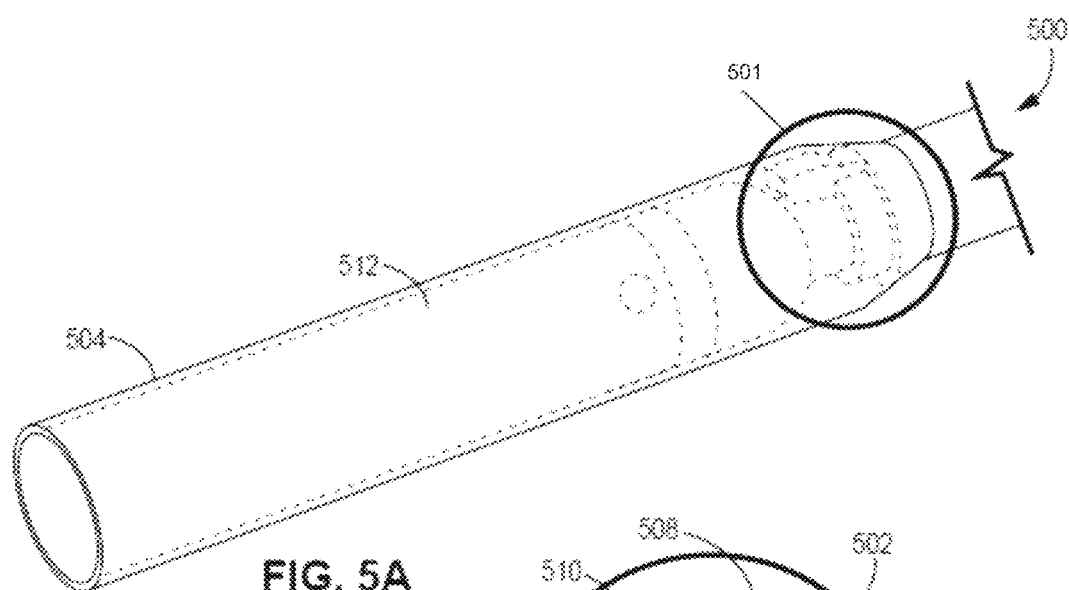
FIGS. 5A-5D are conceptual and schematic diagrams illustrating a distal cup coupled to a distal end of an elongate member of an example catheter.
Figure 5B:
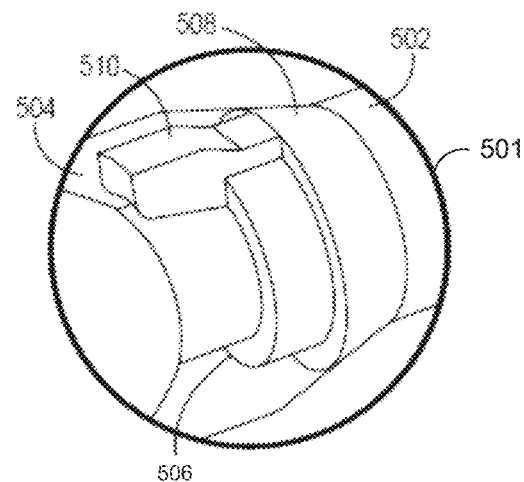
Figure 5C:
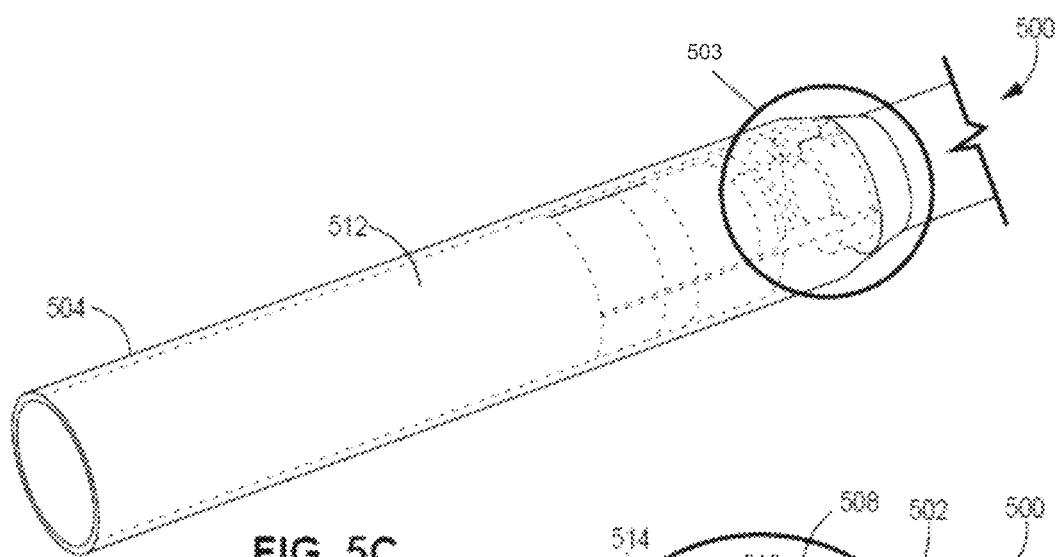
Figure 5D:
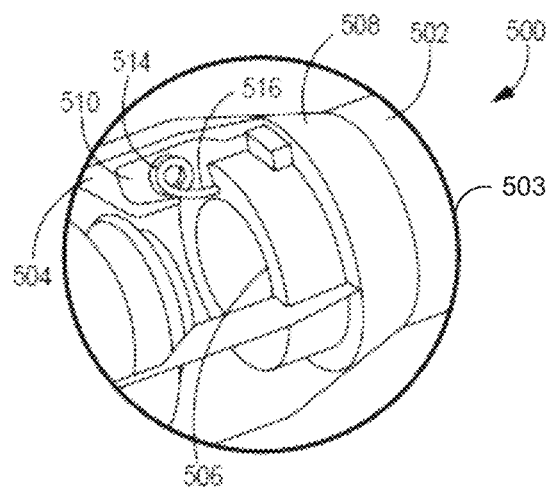

FIGS. 5A-5D are conceptual and schematic diagrams illustrating a distal cup 504 coupled to a distal end 506 of an elongate member 502 of an example catheter 500. For purposes of illustration, distal cup 504 is illustrated as a transparent polymer and, in FIGS. 5C and 5D, with a partial cut away. As shown in FIG. 5A, a reference numeral 501 indicates a portion of catheter 500 illustrated in greater detail by FIG. 5B. As shown in FIG. 5C, a reference numeral 503 indicates a portion of catheter 500 illustrated in greater detail in FIG. 5D. Catheter 500 may be the same as or substantially similar to any one or more of catheters 100, 200, 300, and 400 discussed above in reference to FIGS. 1-4. For example, distal cup 504 may be configured to receive implantable medical device 512. In some examples, distal cup 504 may be overmolded onto distal fixation member 508 and distal end 506 of elongate member 502. By overmolding distal cup 504 onto distal fixation member 508 and distal end 506 of elongate member 502, distal cup 504 may encase fixation arm 510 of distal fixation member 508 to securely retain distal end 514 of pull wire 516. Securely retaining distal end 514 of pull wire 516 may enable pull wire 516 to transfer a push force and/or a pull for to elongate member 502.

Figure 6:
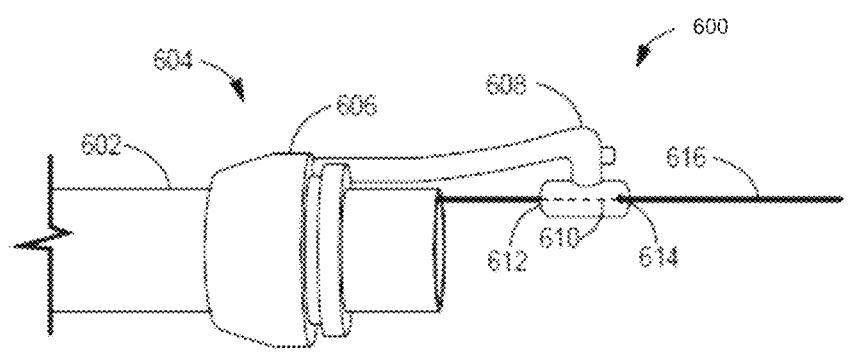
FIG. 6 is a conceptual diagram illustrating a proximal fixation member on a proximal end of an elongate member of an example catheter.

FIG. 6 is a conceptual diagram illustrating a proximal fixation member 606 on a proximal end 604 of an elongate member 602 of an example catheter 600. Catheter 600 may be the same as or substantially similar to any one or more of catheters 100, 200, 300, 400, 500 discussed above in reference to FIGS. 1-5D. Proximal fixation member 606 is coupled to proximal end 604 of an elongate member 602, as discussed above. Proximal fixation member 606 may define a proximal retention channel configured to retain pull wire 616 in sliding engagement and include a retention arm 608. Retention arm 608 extends from proximal fixation member 606 (e.g., the ferrule or the collet of proximal fixation member 206). Retention arm 608 may include a retention channel 610 extending from a distal end 612 to a proximal end 614 thereof at an angle relative to a longitudinal axis of elongate member 602. Retention channel 610 may be configured to retain pull wire 616 in sliding engagement. In this way, proximal fixation member 606 may orient pull wire 616 away from elongate member 602 such that a proximal end of pull wire 208 may be coupled to a control member of a deflection assembly (e.g., control member 114 of deflection assembly 104).

Figure 7A:
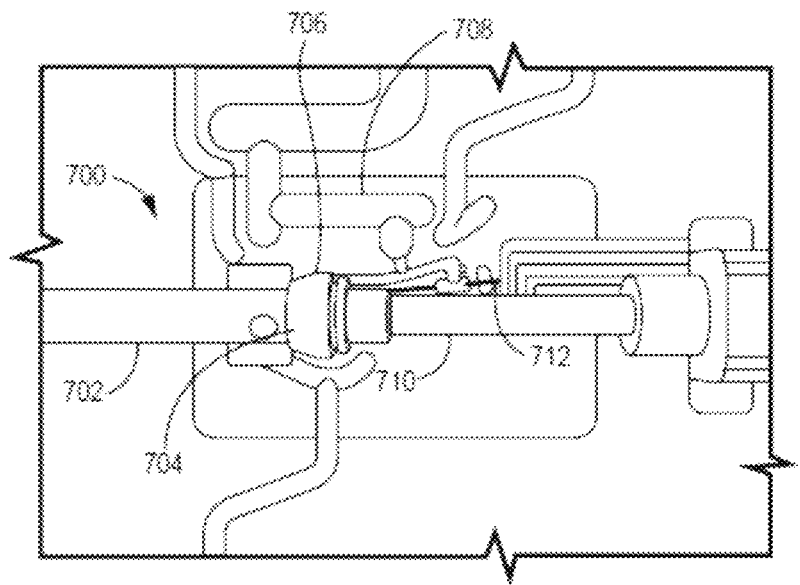
FIGS. 7A and 7B are conceptual diagram illustrating an example mold die for overmolding the proximal fixation member illustrated in FIG. 6 on to an example catheter.
Figure 7B:
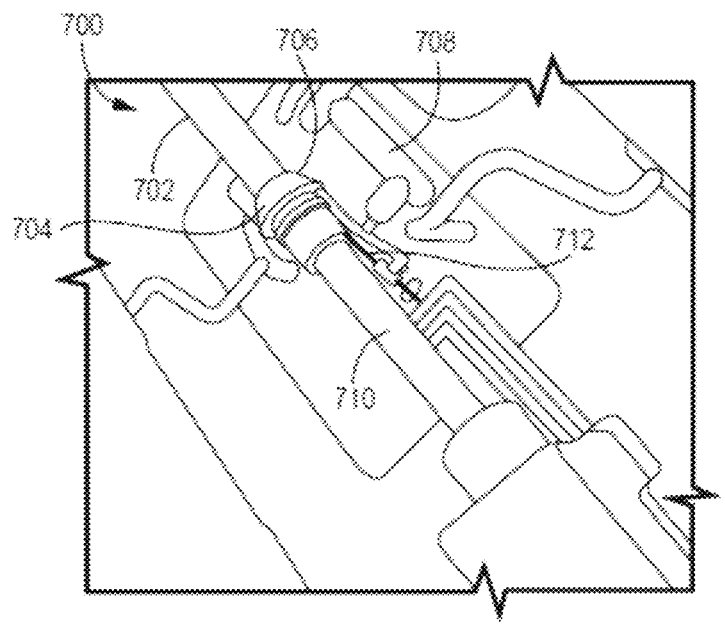

As discussed above, in some examples, a distal fixation member and/or a proximal fixation member may be overmolded onto an elongate member over a pull wire. FIGS. 7A and 7B are conceptual diagrams illustrating an example mold die 700 for overmolding a proximal fixation member 704, such as proximal fixation member 606 illustrated in FIG. 6, onto an elongate member 702 of an example catheter 700. A first half of mold die 700 is illustrated in FIGS. 7A and 7B. A second half of mold die (not shown) is configured to be coupled to the first half of mold die to overmold proximal fixation member 704 onto elongate member 702. Mold die 700 may include a mold region 706 corresponding to a selected shape of proximal fixation member 704 and one or more channels 708 configured to direct an injected flowable polymer into the mold. In some examples, mold die 700 may include a pin 710 configured to fit within the lumen defined by elongate member 702. Pin 710 may reduce deformation, such as collapsing of the lumen, of elongate member 702 when a flowable polymer is injected into mold region 706. Mold die 700 also defines a pull wire channel 712 configured to receive a pull wire extending from a proximal end of elongate member 702. Pull wire channel 712 may extend at an angle from a longitudinal axis of elongate member 702.

Figure 8A:
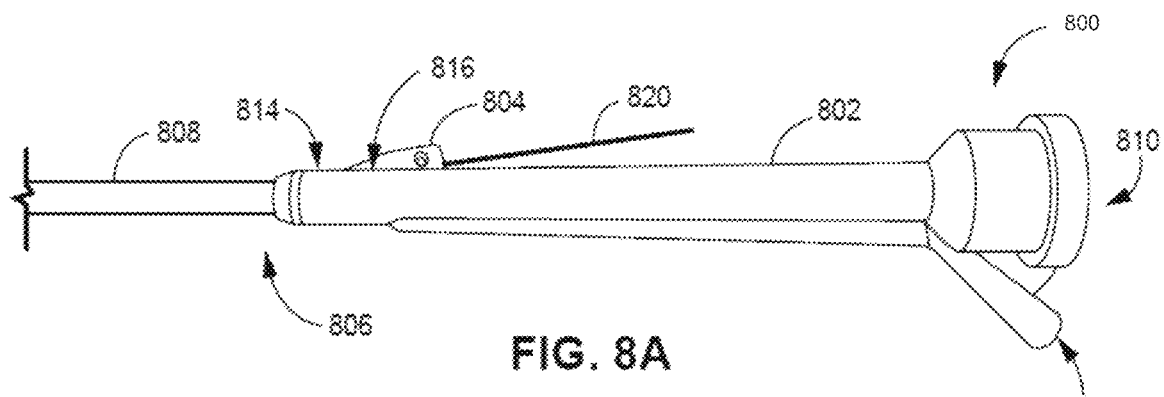
FIGS. 8A-8C are conceptual diagrams illustrating an example hub assembly and an example reveal surround of a catheter.
Figure 8B:
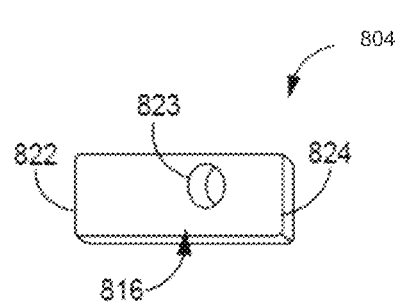
Figure 8C:
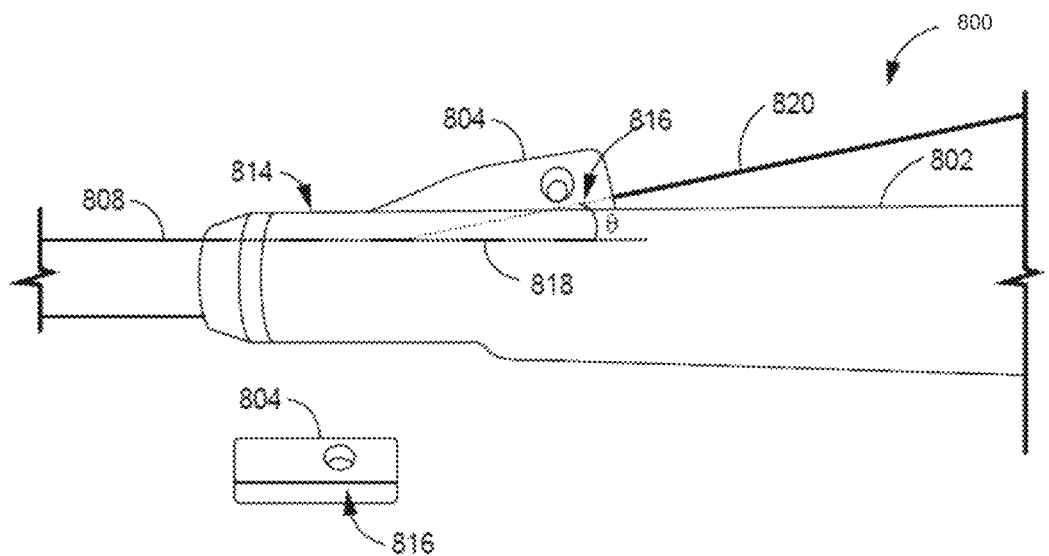

As discussed above, a catheter may include a reveal surround that enables a hub assembly to be overmolded onto at least a portion of proximal portion (e.g., proximal end) of an elongate member of the catheter such that a pull wire of the catheter may be fluidically isolated from a lumen of the catheter. FIGS. 8A-8C are conceptual diagrams illustrating an example hub assembly 802 and an example reveal surround 804 of a catheter 800. Catheter 800 may be the same as or substantially similar to any one or more of catheters 100, 200, 300, 400, 500, 600, 700 discussed above in reference to FIGS. 1-7B. Hub assembly 802 may be overmolded onto proximal portion 806 of elongate member 808. In some examples, a handle of a deflection assembly may be configured to surround and engage at least a portion of hub assembly 802. Hub assembly 802 may define a lumen 810 fluidly coupled to a lumen of elongate member 808. In some examples, hub assembly 802 also may define a flush port 812.

In some examples, reveal surround 804 may be coupled to a proximal fixation member 814 (e.g., the proximal fixation member 814 being coupled to proximal end 806 of elongate member 808). For example, reveal surround 804 may couple to a retention arm of proximal fixation member 814. As illustrated in FIG. 8B, reveal surround 804 may include a reveal surround channel 816 extending from distal end 822 to proximal end 824 and an alignment aperture 823. Reveal surround channel 816 may be configured to retain pull wire 820 in sliding engagement and, when pull wire 820 is positioned within reveal surround channel 816, reduce or prevent passage of fluid through reveal surround channel 816. Alignment aperture 823 may be used to align and secure reveal 804 during overmolding. Additionally, or alternatively, when overmolding hub 802 onto proximal fixation member 814, the hot overmold material connects to the elongate member 808 and/or proximal fixation member 814, and surrounds pull wire 820. When overmolding hub 802, the ferrule of the retention arm (e.g., proximal end ferrule 250) and reveal 804 may prevent the hot overmold material from being expelled from the mold. As illustrated in the magnified view of FIG. 8C, reveal surround channel 816 may extend at angle θ relative to longitudinal axis 818 of elongate member 808. Reveal surround 804 may enable hub assembly 802 to be overmolded onto proximal portion 806 of elongate member 808 such that pull wire 808 is fluidically isolated from lumen 810. In this way, catheter 800 may include a leak resistant or leak proof pull wire assembly. In some examples, a sacrificial wire may be used during molding and then replaced with the final pull wire. This may aid in manufacturing and enhance pull wire ease of movement.

Figure 9A:
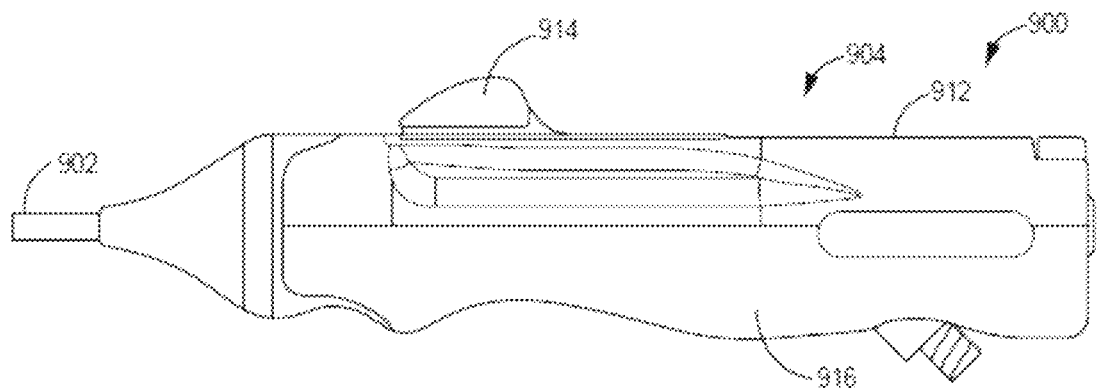
Figure 9B:
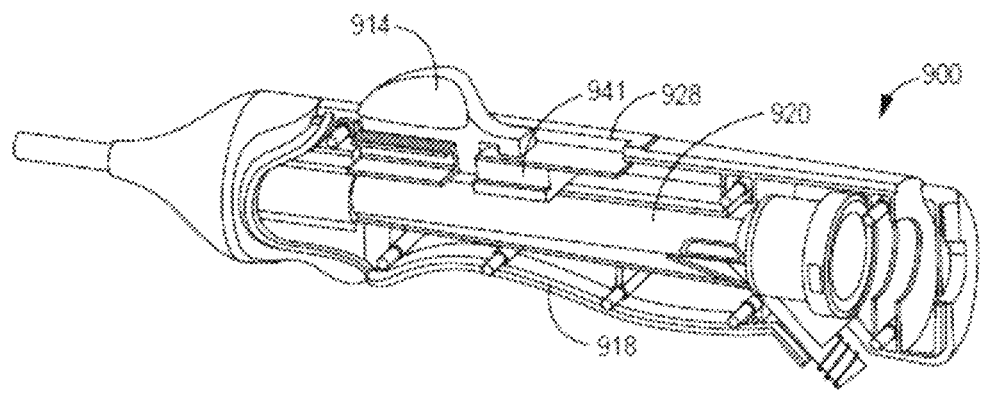
Figure 9C:
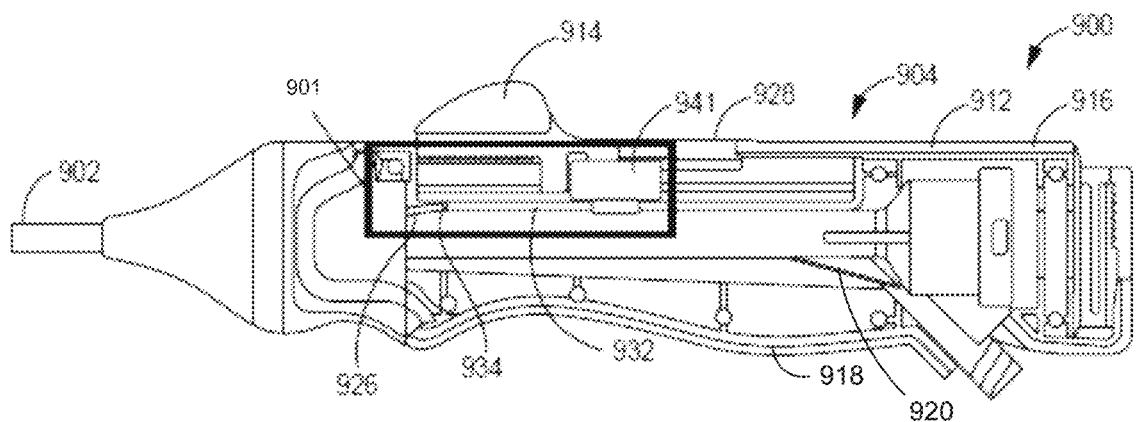
Figure 9D:
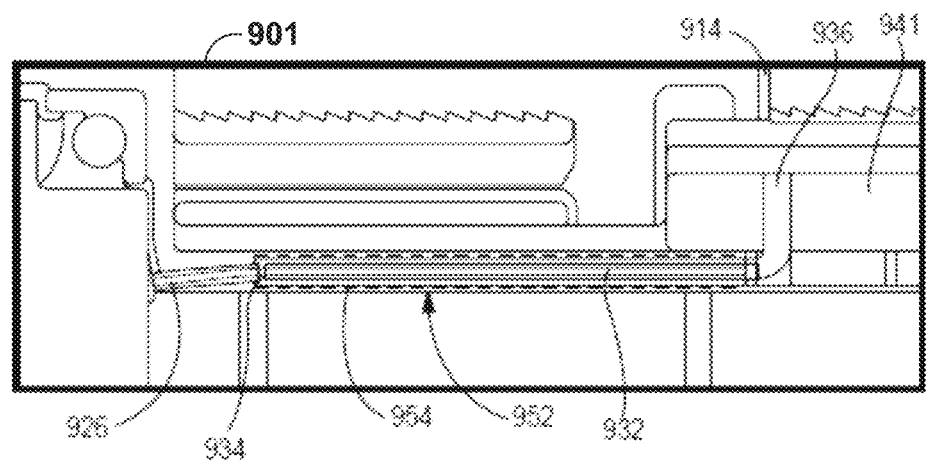

As discussed above, a deflection assembly of a deflectable catheter may include a handle configured to surround and engage at least a portion of the hub assembly and enable a clinician to manipulate the deflectable catheter. FIGS. 9A-9F are conceptual diagrams illustrating an example handle 912 of a deflection assembly 904 of a catheter 900. As shown in FIG. 9C, a reference numberal 901 indicates a portion of catheter 900 illustrated in greater detail FIG. 9D. As shown in FIG 9E, a reference numeral 903 indicates a portion of catheter 900 illustrated in greater detail by FIG. 9F. Catheter 900 may be the same as or substantially similar to any one or more of catheters 100, 200, 300, 400, 500, 600, 700, 800 discussed above in reference to FIGS. 1-8C. As illustrated in FIGS. 9A and 9B, handle 912 may include a first portion 916 and a second portion 918. First and second portions 916 and 918 of handle 912 are configured to mechanically couple to surround at least a portion of hub assembly 920. Deflection assembly 904 also includes control member 914. Control member 914 may be slidably engaged with handle 912. For example, handle 912 may define track 928, along which control member 914 may move (e.g., in the proximal-distal direction). In some examples, control member 914 may be coupled to pull wire 926 via pull block 941.

As illustrated in FIGS. 9C-9F, pull wire 926 may be coupled to control member 914 via hypotube 932 and pull block 941. For example, deflection assembly 904 includes a hypotube 932 extending from a distal end 934 to a proximal end 936. As illustrated in FIG. 9F, pull wire 926 may extend into or through a lumen 931 of hypotube 932. In some examples, hypotube 932 may be crimped onto at least a portion of pull wire 926 to mechanically coupled hypotube 932 to pull wire 926. In some examples, distal end 934 of hypotube 932 may be directly coupled to a proximal portion (e.g., proximal end 930) of pull wire 926. In some examples, hypotube 932 may be bent at roughly 90 degrees to interface with the longitudinally extending pull wire 926 and control member 914 which travels in the longitudinal direction along handle 912.

In some examples, hypotube 932 may be substantially rigid compared to pull wire 926. For example, hypotube 932 may be sufficiently rigid such that, in response to a push force or a pull force applied by a clinician to control member 914, hypotube 932 travels with control member 914 in the proximal-distal direction rather than, for example, deflecting or bending in response to the pull force or push force. Hypotube 932 include any suitable material, such as, for example, stainless steel, nitinol, or a medical grade alloy.

Proximal end 936 of hypotube 932 and/or proximal end 930 of pull wire 926 may be directly coupled to pull block 941. Clearance pocket 940 of control member 914 may allow control member 914 to travel up and down independent of hypotube 932. In this way, control member 914 is coupled to pull wire 926 to transfer a pull force and/or a push force to hypotube 932 and pull wire 926.

Handle 912 is formed to constrain pull wire 926 such that a push force applied to pull wire 926 by control member 914, e.g., via hypotube 932, is transferred along a longitudinal axis of pull wire 926 rather than causing pull wire 926 to bend or kink. The constraint of pull wire 926 may include a plurality of constraint regions. For example, as illustrated in FIG. 9F, a first constraint region 950 may include lumen 931 of hypotube 932. As discussed above, hypotube 932 may be crimped onto a portion of pull wire 926 to support pull wire 926 and enable proximal end 930 of pull wire 926 to be anchored to control member 914. A second constraint region 952 may include handle surround 954. Handle surround 954 may include a channel or tunnel through which pull wire 926 and/or hypotube 932 may freely travel. For example, first and second portions 916 and 918 of handle 912 may be configured to mate to define handle surround 952. A third constraint region 956 may include proximal fixation member 922 (e.g., including retention arm 923) and reveal surround 924. As discussed above, proximal fixation member 922 and reveal surround 924 may define at least a portion of an area between where pull wire 926 extends through wall 910 of the elongate member 902 and connects to hypotube 932. For example, proximal fixation member 922 may encase pull wire 926 from a point where pull wire 926 extends through wall 910 of elongate body 902 to reveal surround 924. Reveal surround 924 may enable overmolding of hub assembly 920 and the pull wire to extend to the hypotube. In this way, first, second, and third constraints 950, 952, and 956 enable active return of elongate tube 902.

Figure 10A:
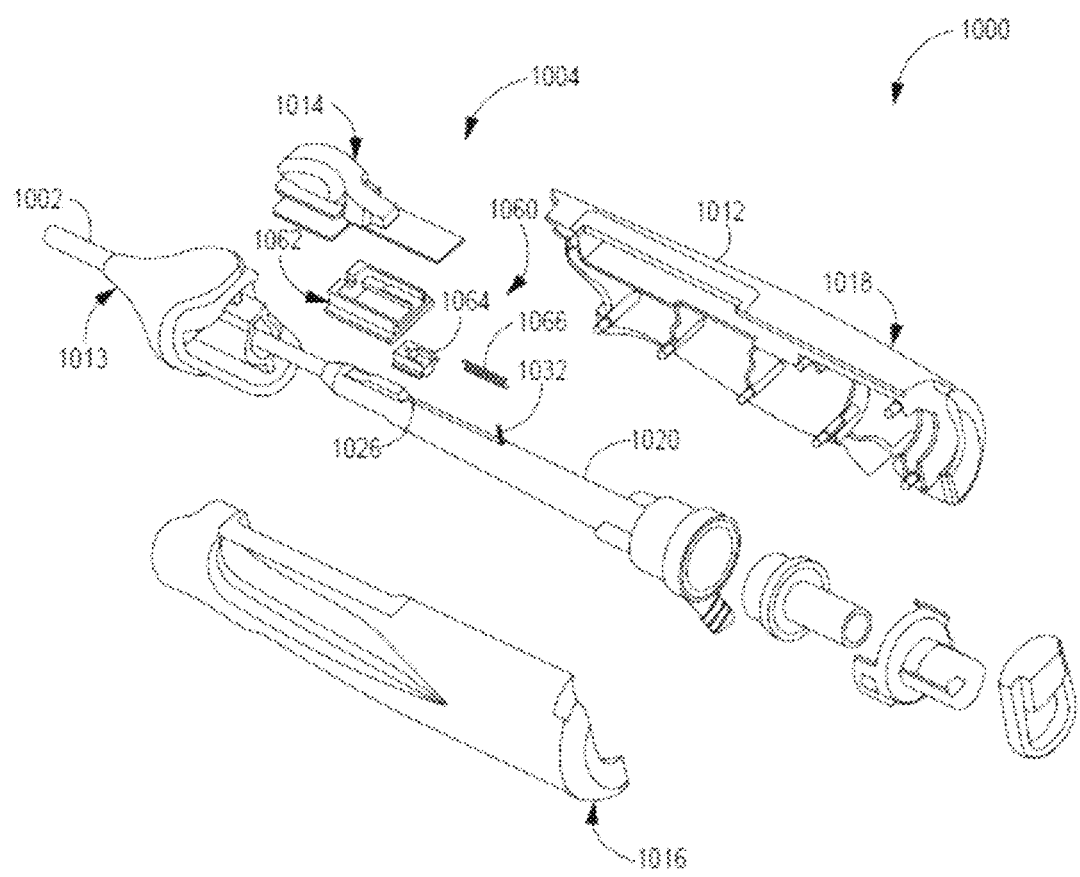
FIGS. 10A-10C are conceptual diagrams illustrating an example deflectable catheter having deflection assembly including a dampening member.
Figure 10B:
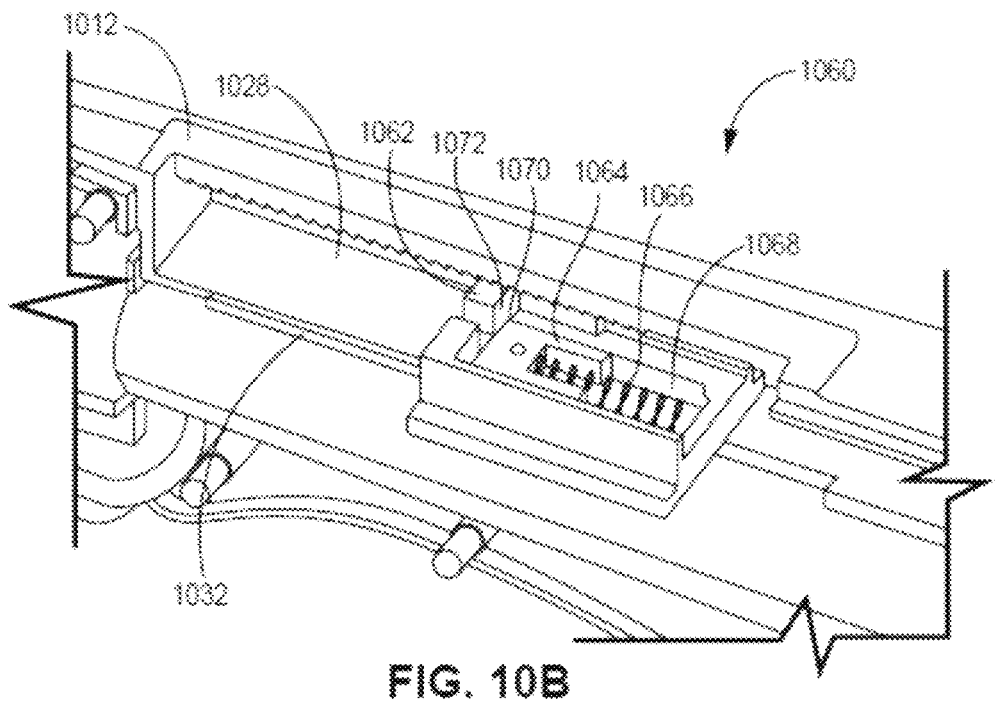

In some examples, a deflection assembly of a deflectable catheter may include a dampening member configured to dampen a force applied to control member 114 in a distal direction, a proximal direction, or both. FIGS. 10A-10B are conceptual diagrams illustrating an example deflectable catheter 1000 having deflection assembly 1004 including a dampening member 1060. Catheter 1000 may be the same as or substantially similar to any one or more of catheters 100, 200, 300, 400, 500, 600, 700, 800, 900 discussed above in reference to FIGS. 1-9F. As illustrated in the exploded view of FIG. 10A, deflection assembly 1004 includes handle 1012, strain relief member 1013, control member 1014, hub assembly 1020, and dampening member 1060. Handle 1012 includes a first portion 1016 and a second portion 1018 that are configured to mechanically couple to surround at least a portion of hub assembly 1020, e.g., to define a handle surround. Strain relief member 1013 may be configured to couple to first and second portions 1016 and 1018 of handle 1012 and to at least a portion of elongate member 1002 to enable handle 1012 to transfer a movement of handle 1012 to elongate member 1002, such as, for example, a torque or proximal-distal movement of handle 1012. As discussed above, handle 1012 may couple to hub assembly 1020. Pull wire 1026 may be coupled to hypotube 1032, which is configured to couple to control member 1014.

Figure 10C:
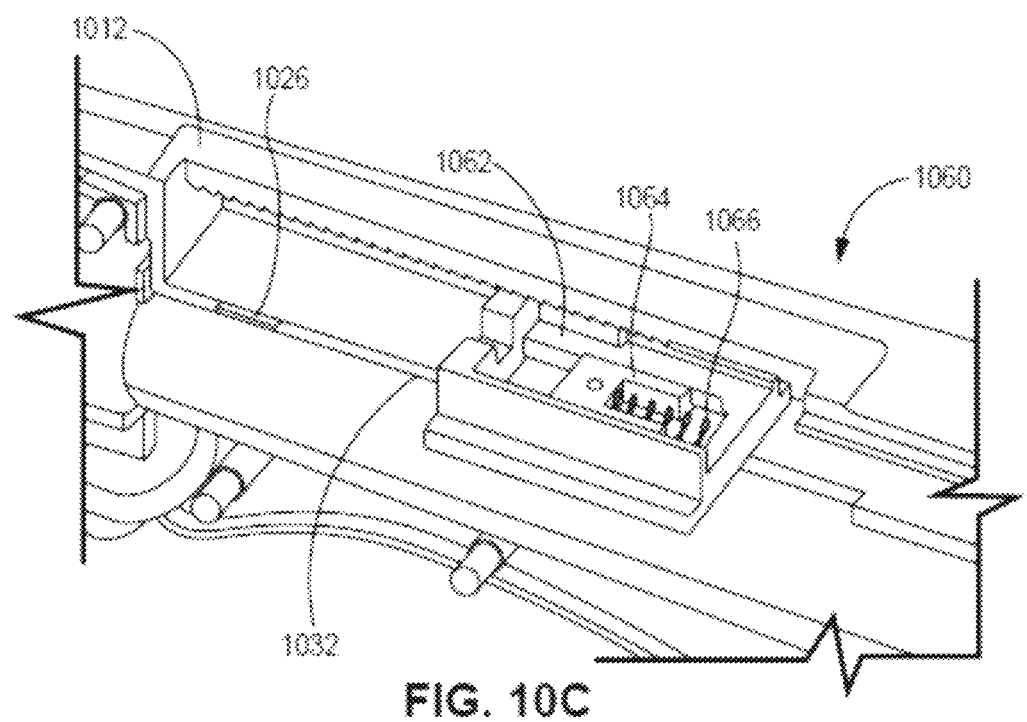

Dampening member 1060 is configured to dampen a force applied to control member 1014 in a distal direction, a proximal direction, or both. Dampening member 1060 may include an outer pull block 1062, an inner pull block 1064, and a spring 1066. Outer pull block 1062 may be configured to couple to control member 1014. Outer pull block 1062 may be in sliding engagement with track 1028 defined by handle 1012. For example, when a clinician moves control member 1014 in the proximal-distal direction, outer pull block 1062 may move with control member 1014 (e.g., the same direction and distance). Outer pull block 1062 may define a track 1068 in sliding engagement with inner pull block 1064. Inner pull block 1064 may be coupled to hypotube 1032 which is coupled to pull wire 1026. As illustrated in FIG. 10B, when control member 1014 is moved in a proximal direction, a distal surface 1070 of inner pull block 1064 may contact a distal wall 1072 of outer pull block 1062. In this way, inner pull block 1064 may move with outer block 1062 when control member 1014 is moved in a proximal direction. As illustrated in FIG. 10C, when control member 1014 is moved in a distal direction (e.g., active return), inner pull block 1064 may resist movement relative to outer pull block 1062 such that movement of control member 1014 and outer pull block 1062 in the distal direction may result in the compression of spring 1066. In this way, when control member 1014 is pulled proximally spring 1066 is not engaged (under compression or tension), but when control member 1014 is pushed distally spring 1066 is engaged under compression (e.g., to act as a shock absorber). Once the force of compression of spring 1066 is greater than the force required for active return of elongate member 1002 (or once a proximal end of inner pull block 1064 contacts a proximal wall of outer pull block 1062) a push force may be transferred from control member 1014 to outer pull bock 1062, through spring 1066 and inner pull block 1064 to hypotube 1032 and pull wire 1026. In this way, catheter 1000 may be configured to dampen a push force applied to control member 1014 during an active return of elongate member 1002. In some examples, the spring also may provide for some active straightening. With no spring 1066, the catheter may function without active straightening.

Figure 11:
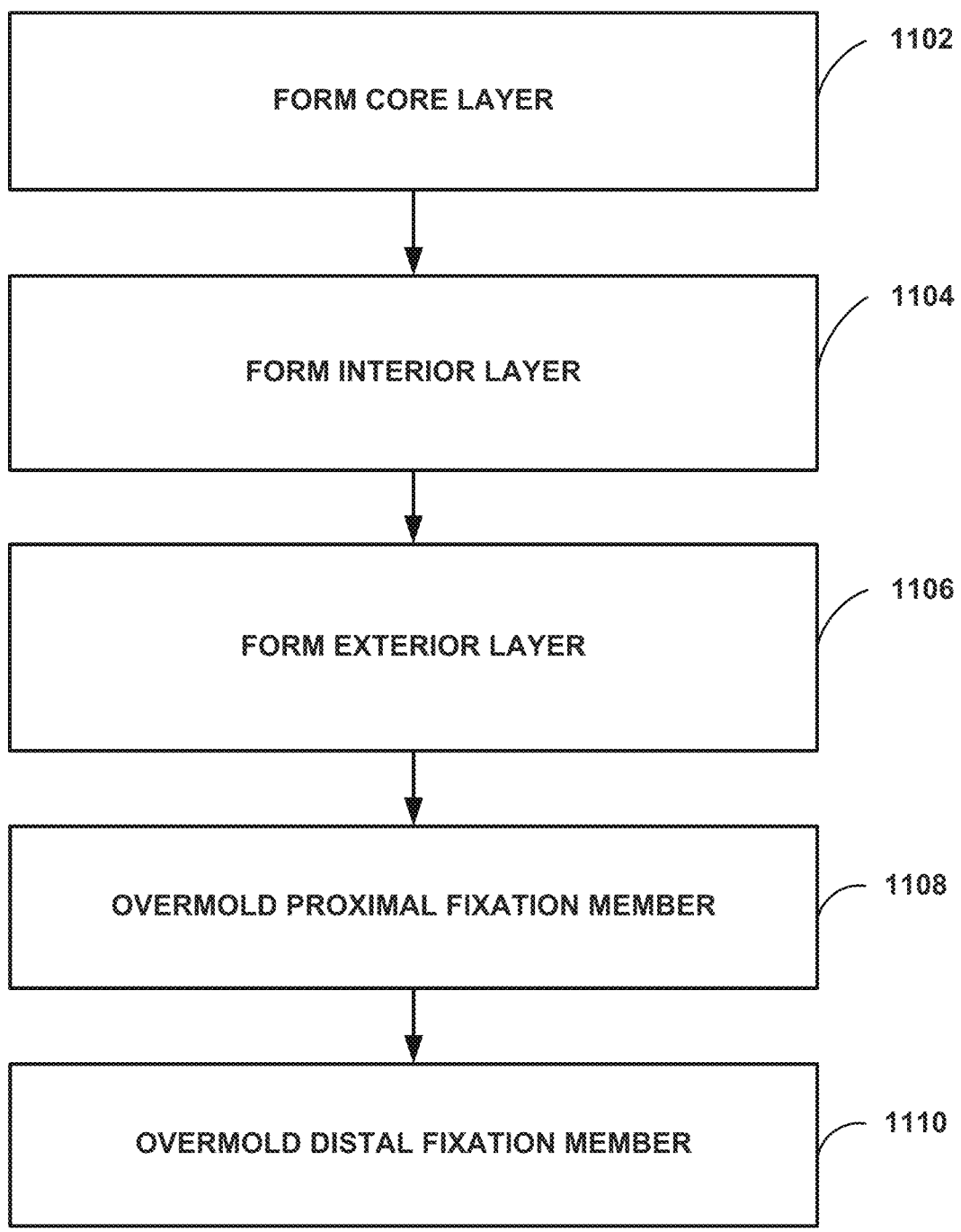
FIG. 11 is a flow diagram illustrating an example method of manufacturing an elongate member of a deflectable catheter.

The catheters described herein may be manufactured using any suitable technique. FIG. 11 is a flow diagram illustrating an example method of manufacturing an elongate member of a deflectable catheter. Although the technique illustrated in FIG. 11 is described in reference to catheter 200 illustrated in reference to FIGS. 2A and 2B, the technique may be used to manufacture other catheters, such as catheters 100, 300, 400, 500, 600, 700, 800, 900, and/or 1000. Additionally, catheters 100, 200, 300, 400, 500, 600, 700, 800, 900, and/or 1000 may be manufactured using other techniques.

The technique illustrated in FIG. 11 includes forming elongate member 202. Forming elongate member may include, for example, forming a core layer 218 (1102), forming an interior layer, e.g., an inner layer 224 (1104), and forming an exterior layer, e.g., an outer layer 226 (1106). Forming elongate member may also include, for example, positioning inner layer 224 over a mandrel, positioning a sacrificial pull wire on inner layer 224, positioning a tubular member over the sacrificial pull wire and inner layer 224, positioning core layer 218 over the tubular member, and positioning outer layer 226 over the core layer 218. As discussed above, inner layer 224 may include any suitable polymer, such as, for example, polytetrafluoroethylene. As discussed above, outer layer 226 may include any suitable polymer, such as, for example, polyether block amide.

In some examples, positioning core layer 218 may include braiding two or more metal wires onto a mandrel. In some examples, forming core layer 218 may include forming core layer 218 directly over inner layer 224. In some examples, forming elongate core layer 218 may include abrading or coating an interior surface of an exterior surface of elongate core layer 218 prior to depositing inner layer 224 or outer layer 226 on a respective surface.

In some examples, rather than positioning core layer 218 on inner layer 224, the technique may include depositing onto interior surface 222 of core layer 218 a polymer to form inner layer 224. Any suitable deposition or coating method may be used to deposit inner layer 224. In some examples, inner layer 224 may be deposited onto a mandrel prior to forming elongate core layer 218 over inner layer 224. In some examples, pull wire 208 (or a sacrificial wire) may be positioned adjacent to interior surface 222 of core layer 218 prior to depositing inner layer 224 such that inner layer 224 may substantially encase pull wire 208.

In some examples, rather than positioning outer layer 226 over core layer 218, the technique may include depositing a polymer onto exterior surface 220 of core layer 218 to form outer layer 226. Any suitable deposition or coating method may be used to deposit outer layer 226. Outer layer 226 may at least partially flow into spaces between filars of core layer 218.

The technique illustrated in FIG. 11 includes overmolding proximal fixation member 206 onto proximal portion 236 of elongate member 202 (1108). In some examples, proximal fixation member 206 (e.g., retention arm 244) may be overmolded to encase at least a portion of pull wire 208. In some examples, the technique may include coupling a reveal surround 252 to retention arm 244. In some examples, the technique also may include overmolding a hub assembly onto proximal fixation member 206 and/or a proximal portion 236 of elongate member 202 thereby encasing the pull wire 208. In examples in which inner layer 224 is deposited over a sacrificial wire, the technique may include, after overmolding proximal fixation member 206, and, in some examples, hub assembly 802, replacing the sacrificial wire with pull wire 208. In some examples, after removing the sacrificial wire, e.g., by pulling, a proximal end of pull wire 208 may be threaded into inner layer 224 at the distal end 212 of elongate body 202. In some example, the distal end 232 of pull wire 208 may include a bulbous structure that may be anchored to distal fixation member 204.

The technique illustrated in FIG. 11 includes overmolding distal fixation member 204 onto distal portion 230 of elongate member 202 (1110). In some examples, distal fixation member 204 may be overmolded to encase at least a portion of distal end 232 of pull wire 208. In some examples, before or after overmolding distal fixation member 204, the technique may include knotting, looping, and/or welding a bulbous structure to distal end 232 of pull wire 208. In some examples, the technique also may include overmolding a distal cup onto distal fixation member 204 and/or a distal portion 230 of elongate member 202.

Figure 12:
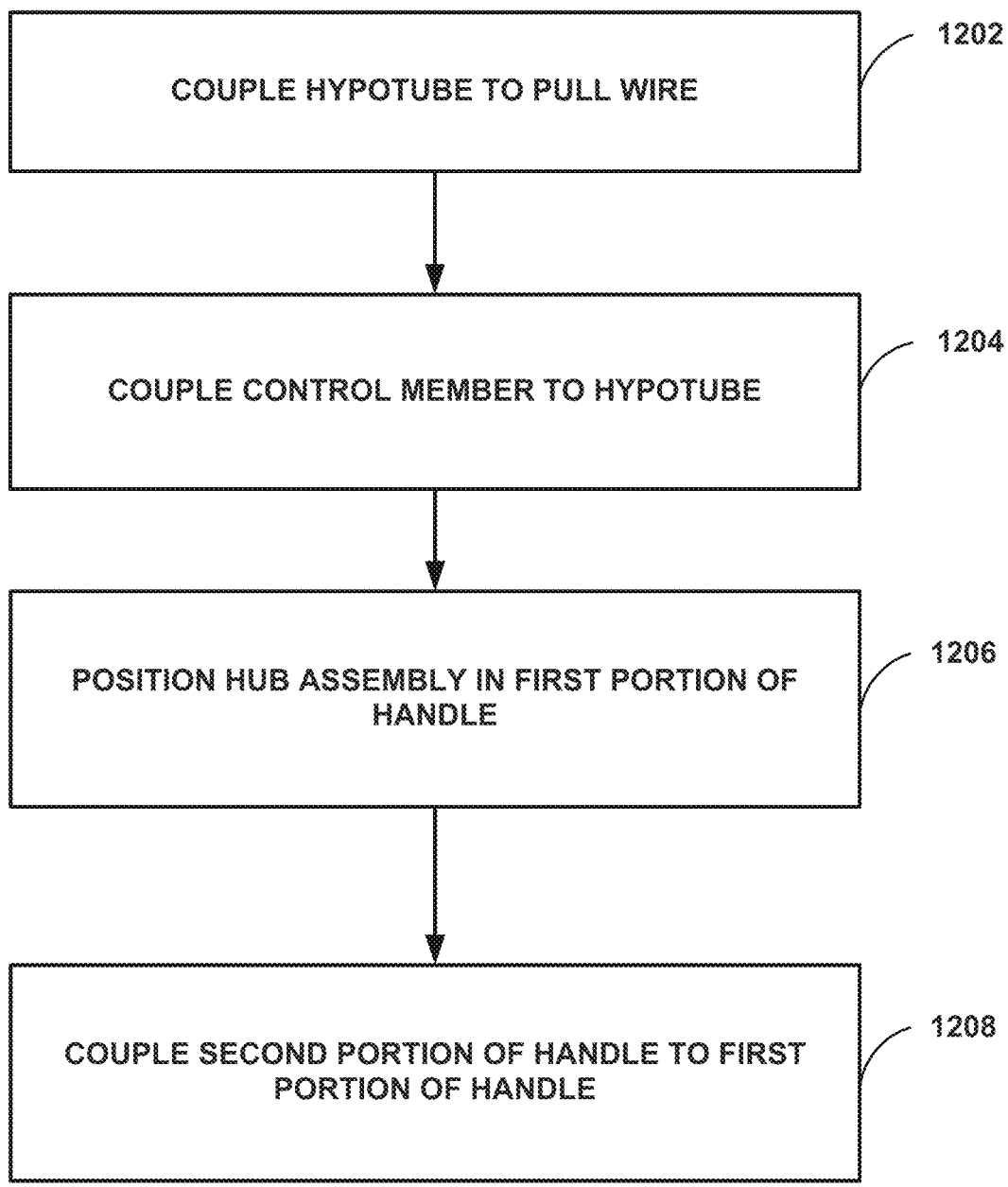
FIG. 12 is a flow diagram illustrating an example method of manufacturing a deflectable assembly of a deflectable catheter.

FIG. 12 is a flow diagram illustrating an example method of manufacturing a deflectable assembly of a deflectable catheter. Although the technique illustrated in FIG. 12 is described in reference to catheter 900 illustrated in reference to FIGS. 9A-9F, the technique may be used to manufacture other catheters, such as catheters 100, 200, 300, 400, 500, 600, 700, 800, and/or 1000. Additionally, catheters 100, 300, 400, 500, 600, 700, 800, 900, and/or 1000 may be manufactured using other techniques.

The technique illustrated in FIG. 12 includes coupling hypotube 932 to pull wire 926 (1202). For example, pull wire 926 may be positioned within a lumen 931 of hypotube 932 and then hypotube 932 may be crimped to mechanically coupled hypotube 932 to pull wire 926. In other examples, pull wire 926 may be adhered to hypotube 932, for example, using an epoxy or another suitable adhesive or welding.

The technique illustrated in FIG. 12 includes coupling control member 914 to hypotube 932 (1204). For example, hypotube 932 may be mechanically coupled into a molded fitting defined by control member 914 or adhered to control member 914, for example, using an epoxy or another suitable adhesive. In examples in which the catheter includes a dampening member, the technique may include assembling dampening member 1060, coupling inner pull block 1064 to hypotube 1032, and coupling outer pull block 1062 to control member 1014.

The technique illustrated in FIG. 12 includes positioning elongate member 902 and/or hub assembly 920 on first portion 916 of handle 912 (1206). The technique also includes coupling second portion 918 of handle 912 to first portion 916 (1208).

Figure 13:
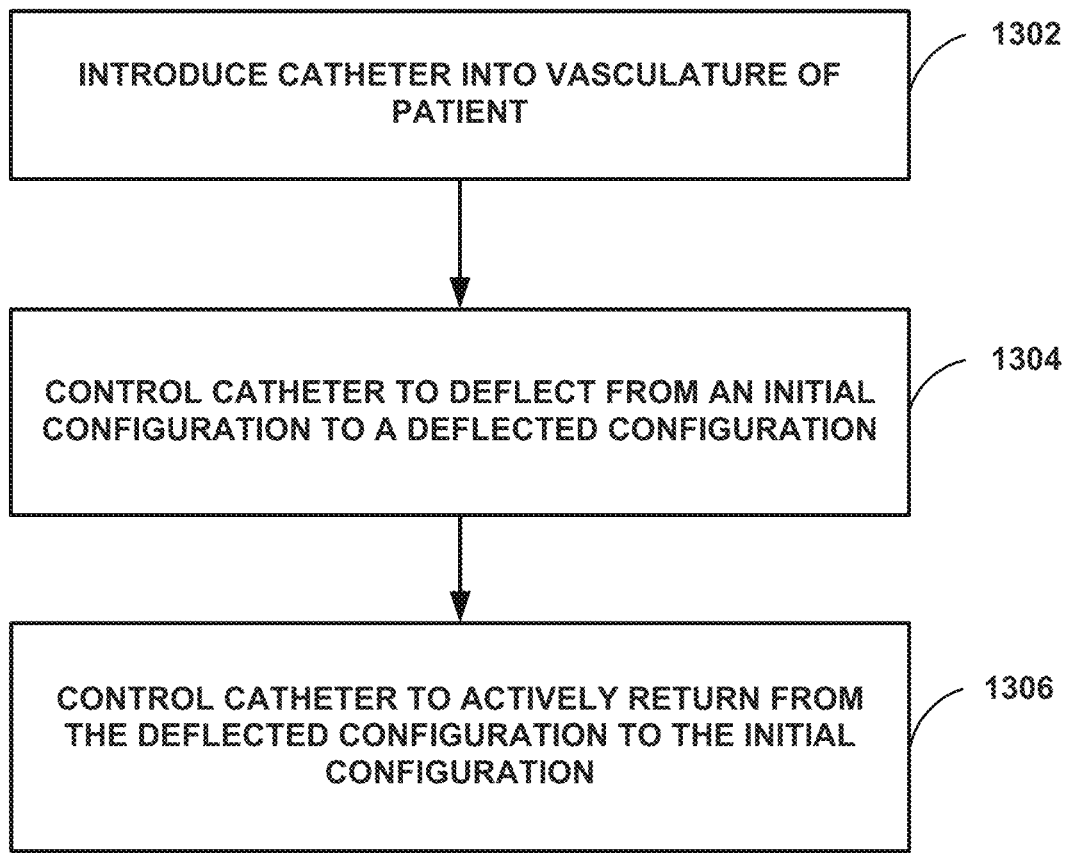
FIG. 13 is a flow diagram illustrating an example method of using a deflectable catheter.

The catheters described herein may be used to delivery an implantable medical device to a target site within a body of a patient. FIG. 13 is a flow diagram illustrating an example method of using a deflectable catheter. Although the technique illustrated in FIG. 13 is described in reference to catheter 100 illustrated in reference to FIG. 1, the technique may be used with other catheters, such as catheters 200, 300, 400, 500, 600, 700, 800, 900, and/or 1000. Additionally, catheters 100, 200, 300, 400, 500, 600, 700, 800, 900, and/or 1000 may be used with other techniques.

The technique illustrated in FIG. 13 includes introducing distal portion 116 of elongate body 102 of catheter 100 into vasculature of a patient (1302). In some examples, introducing catheter 100 may include creating an incision in the femoral vein of the patient.

After introducing catheter 100, the technique may include navigating catheter 100 to a target chamber of the heart of the patient. In some examples, navigating may include using fluoroscopy to visualize a location of catheter 100 relative to an anatomy of the patient. Navigating catheter 100 includes controlling catheter 100 to deflect from an initial configuration to a deflected configuration (1304), and controlling catheter 100 to actively return from the deflected configuration to the initial configuration (1306). The technique also may include deploying an IMD from a distal cup 134 of catheter 100 to the target location within the vasculature of the patient.

The following clauses illustrate example subject matter described herein.

Clause 1. A catheter comprising: an elongate member extending from a proximal end to a distal end, wherein the elongate member comprises a wall defining a longitudinally extending lumen; a fixation member coupled to an exterior surface of the wall on a distal portion of the elongate member; and a pull wire extending through the wall of the elongate member from the proximal end of the elongate member to the fixation member, wherein the pull wire is coupled to the fixation member, and wherein the elongate member is configured to deflect from an initial configuration to a deflected configuration in response to a pull force applied to the pull wire.

Clause 2. The catheter of claim 1, wherein the elongate member is further configured to deflect from the deflected configuration to the initial configuration in response to a push force applied to the pull wire.

Clause 3. The catheter of claim 1 or 2, wherein the pull wire extends from the proximal end of the elongate member to the fixation member through at least a portion of the wall of the elongate member.

Clause 4. The catheter of any one of claims 1 through 3, wherein the wall comprises: an elongate core layer defining an exterior surface and an interior surface defining the longitudinally extending lumen; an inner layer disposed on the interior surface of the elongate core layer; and an outer layer disposed on the exterior surface of the elongate core layer, wherein the pull wire is disposed at least one of between the inner layer and the core layer or through the inner layer.

Clause 5. The catheter of claim 4, wherein the elongate core layer comprises a coiled or braided metal wire.

Clause 6. The catheter of claim 4 or 5, wherein the pull wire protrudes through the core layer and the outer layer to an exterior surface of the outer layer at a proximal portion of the elongate member.

Clause 7. The catheter of any one of claims 1 through 6, wherein the fixation member comprises at least one of a ferrule or a collet configured to engage the exterior surface of the wall of the elongate member by at least one of a friction fit, a compression fit, or an overmold and couple to a distal end of the pull wire.

Clause 8. The catheter of any one of claims 1 through 7, wherein a distal end of the pull wire comprises at least one of a bulbous structure, a loop, a knot, a weld bead, or a washer.

Clause 9. The catheter of any one of claims 1 through 8, wherein a distal end of the catheter comprises a distal cup extending from the fixation member to a distal tip of the distal cup, wherein the distal cup encases at least one of at least a portion of the fixation member or at least a portion of the distal end of the elongate pull wire.

Clause 10. The catheter of claim 9, wherein the elongate member comprises a first polymer, wherein the distal cup comprises a second polymer, and wherein at least one of a tensile strength of the second polymer is greater than a tensile strength of the first polymer or a ductility of the first polymer is greater than a ductility of the second polymer.

Clause 11. The catheter of any one of claims 1 through 10, wherein the fixation member comprises a first fixation member, and the catheter further comprises a second fixation member is coupled to an exterior surface of the wall on the proximal end of the elongate member.

Clause 12. The catheter of claim 11, wherein the second fixation member comprises: at least one of a ferrule or a collet configured to engage the exterior surface of the wall of the elongate member by at least one of a friction fit or a compression fit; and a channel configured to retain the pull wire in sliding engagement.

Clause 13. The catheter of claim 12, wherein the second fixation member further comprises a retention arm extending from the ferrule or the collet, the retention arm comprising a retention channel extending from a distal end to a proximal end thereof at an angle away from a longitudinal axis of the elongate member, wherein the retention channel is configured to retain the pull wire in sliding engagement.

Clause 14. The catheter of claim 13, wherein the second fixation member further comprises a reveal surround coupled to the retention arm, the reveal surround comprising a reveal surround channel configured to retain the pull wire in sliding engagement, wherein the reveal surround channel extends from a distal end to a proximal end thereof at an angle away from the longitudinal axis of the elongate member.

Clause 15. The catheter of any one of claims 1 through 14, wherein the catheter further comprises an overmolded hub assembly encasing at least a proximal portion of the elongate member.

Clause 16. The catheter of claim 15, wherein the overmolded hub assembly encases at least a portion of the second fixation member and at least a distal portion of the reveal surround.

Clause 17. A catheter comprising: an elongate member extending from a proximal end to a distal end, wherein the elongate member comprises a wall defining a longitudinally extending lumen; a distal fixation member coupled to an exterior surface of the wall on a distal portion of the elongate member; a proximal fixation member coupled to an exterior surface of the wall on a proximal portion of the elongate member; a retention arm integrally formed with the proximal fixation member, wherein the retention arm is configured to retain the pull wire in sliding engagement at an angle extending away from a longitudinal axis of the elongate member; and a pull wire extending from a distal end coupled to the distal fixation member, through the wall of the elongate member, to a distal portion extending through the proximal fixation member and retention arm, and wherein the elongate member is configured to deflect from an initial configuration to a deflected configuration in response to a pull force applied to the pull wire.

Clause 18. A method comprising: forming an elongate member extending from a proximal end to a distal end, wherein the elongate member comprises a wall defining a longitudinally extending lumen; overmolding a fixation member onto an exterior surface of the wall on a distal portion of the elongate member; and anchoring a pull wire to the fixation member, wherein the pull wire extends through the wall of the elongate member from the proximal end of the elongate member to the fixation member, and wherein the elongate member is configured to deflect from an initial configuration to a deflected configuration in response to a pull force applied to the pull wire.

Clause 19. The method of claim 18, wherein forming the elongate member comprises: positioning the pull wire adjacent to an exterior surface of an elongate core layer of the elongate member; and forming an outer layer on an exterior surface of the elongate core layer, wherein the pull wire extends through the outer layer from the proximal end of the elongate member to the fixation member.

Clause 20. The method of claim 18 or 19, wherein anchoring the pull wire to the fixation member comprises at least one of knotting or looping a distal end of the pull wire, welding a bulbous structure to the distal end of the pull wire, or overmolding the fixation member to encase the distal end of the pull wire.

Clause 21. The method of any one of claims 18 through 20, wherein anchoring the pull wire to the fixation member comprises overmolding a distal cup to onto at least one of a portion of the fixation member, a distal end of the pull wire, or the distal end of the elongate member.

Clause 22. The method of any one of claims 18 through 21, wherein the fixation member comprises a first fixation member, and wherein the method further comprises overmolding a second fixation member onto an exterior surface of the wall on the proximal end of the elongate member to encase at least a portion of the pull wire.

Clause 23. The method of claim 22, further comprising: coupling a reveal surround to the second fixation member; and overmolding a hub assembly onto at least one of a proximal portion of the second fixation member, a distal portion of the reveal surround, or the proximal portion of the elongate member.

Clause 24. The method of any one of claims 18 through 23, wherein the elongate member is configured to deflect from the deflected configuration to the initial configuration in response to a push force applied to the pull wire.

Various examples of the disclosure have been described. Any combination of the described systems, operations, or functions is contemplated. These and other examples are within the scope of the following claims.

What is claimed is:

1. A catheter comprising:
   an elongate member extending from a proximal end to a distal end, wherein the elongate member comprises a wall defining a longitudinally extending lumen;
   a first fixation member coupled to an exterior surface of the wall on a distal portion of the elongate member;
   a second fixation member coupled to an exterior surface of the wall on the proximal end of the elongate member;
   an overmolded hub assembly encasing at least a proximal portion of the elongate member, wherein the overmolded hub assembly encases at least a portion of the second fixation member and at least a distal portion of a reveal surround; and
   a pull wire extending through the wall of the elongate member from the proximal end of the elongate member to the first fixation member, wherein the pull wire is coupled to the first fixation member, and wherein the elongate member is configured to deflect from an initial configuration to a deflected configuration in response to a pull force applied to the pull wire.

2. The catheter of claim 1, wherein the elongate member is further configured to deflect from the deflected configuration to the initial configuration in response to a push force applied to the pull wire.

3. The catheter of claim 1, wherein the pull wire extends from the proximal end of the elongate member to the first fixation member through at least a portion of the wall of the elongate member.

4. The catheter of claim 1, wherein the wall comprises:
   an elongate core layer defining an exterior surface and an interior surface defining the longitudinally extending lumen;
   an inner layer disposed on the interior surface of the elongate core layer; and
   an outer layer disposed on the exterior surface of the elongate core layer, wherein the pull wire is disposed between the inner layer and the core layer, through the inner layer, or both.

5. The catheter of claim 4, wherein the elongate core layer comprises a coiled or braided metal wire.

6. The catheter of claim 4, wherein the pull wire protrudes through the core layer and the outer layer to an exterior surface of the outer layer at the proximal portion of the elongate member.

7. The catheter of claim 1, wherein the first fixation member comprises a ferrule or a collet configured to:
engage the exterior surface of the wall of the elongate member by at least one selected from a group of a friction fit, a compression fit, and an overmold; and
couple to a distal end of the pull wire.

8. The catheter of claim 1, wherein a distal end of the pull wire comprises at least one selected from a group of a bulbous structure, a loop, a knot, a weld bead, and a washer.

9. The catheter of claim 1, wherein a distal end of the catheter comprises a distal cup extending from the first fixation member to a distal tip of the distal cup, wherein the distal cup encases at least a portion of the first fixation member, at least a portion of a distal end of the pull wire, or both.

10. The catheter of claim 9,
wherein the elongate member comprises a first polymer,
wherein the distal cup comprises a second polymer, and
wherein a tensile strength of the second polymer is greater than a tensile strength of the first polymer, a ductility of the first polymer is greater than a ductility of the second polymer, or both.

11. The catheter of claim 1, wherein the second fixation member comprises:
a ferrule or a collet configured to engage the exterior surface of the wall of the elongate member by a friction fit, a compression fit, or both; and
a channel configured to retain the pull wire in sliding engagement.

12. The catheter of claim 11, wherein the second fixation member further comprises a retention arm extending from the ferrule or the collet, the retention arm comprising a retention channel extending from a distal end to a proximal end thereof at an angle away from a longitudinal axis of the elongate member, wherein the retention channel is configured to retain the pull wire in sliding engagement.

13. The catheter of claim 12, wherein the second fixation member further comprises a reveal surround coupled to the retention arm, the reveal surround comprising a reveal surround channel configured to retain the pull wire in sliding engagement, wherein the reveal surround channel extends from a distal end to a proximal end thereof at an angle away from the longitudinal axis of the elongate member.

14. A catheter comprising:
an elongate member extending from a proximal end to a distal end, wherein the elongate member comprises a wall defining a longitudinally extending lumen;
a distal fixation member coupled to an exterior surface of the wall on a distal portion of the elongate member;
a proximal fixation member coupled to an exterior surface of the wall on a proximal portion of the elongate member;
an overmolded hub assembly encasing at least the proximal portion of the elongate member, wherein the overmolded hub assembly encases at least a portion of the proximal fixation member and at least a distal portion of a reveal surround;
a retention arm integrally formed with the proximal fixation member, wherein the retention arm is configured to retain a pull wire in sliding engagement at an angle extending away from a longitudinal axis of the elongate member; and
the pull wire extending from a distal end to a proximal end,
wherein the distal end of the pull wire is coupled to the distal fixation member,
wherein the pull wire extends through the wall of the elongate member, the proximal fixation member, and the retention arm, and
wherein the elongate member is configured to deflect from an initial configuration to a deflected configuration in response to a pull force applied to the pull wire.

15. A catheter comprising:
an elongate member extending from a proximal end to a distal end, wherein the elongate member comprises a wall defining a longitudinally extending lumen;
a first fixation member coupled to an exterior surface of the wall on a distal portion of the elongate member;
a second fixation member coupled to an exterior surface of the wall on the proximal end of the elongate member, wherein the second fixation member comprises:
a ferrule or a collet configured to engage the exterior surface of the wall of the elongate member by a friction fit, a compression fit, or both;
a channel configured to retain a pull wire in sliding engagement;
a retention arm extending from the ferrule or the collet, the retention arm comprising a retention channel extending from a distal end to a proximal end thereof at an angle away from a longitudinal axis of the elongate member, wherein the retention channel is configured to retain the pull wire in sliding engagement; and
a reveal surround coupled to the retention arm, the reveal surround comprising a reveal surround channel configured to retain the pull wire in sliding engagement, wherein the reveal surround extends from a distal end to a proximal end thereof at an angle away from the longitudinal axis of the elongate member; and
the pull wire extending through the wall of the elongate member from the proximal end of the elongate member to the first fixation member, wherein the pull wire is coupled to the first fixation member, and wherein the elongate member is configured to deflect from an initial configuration to a deflected configuration in response to a pull force applied to the pull wire.

16. The catheter of claim 15, wherein the elongate member is further configured to deflect from the deflected configuration to the initial configuration in response to a push force applied to the pull wire.

17. The catheter of claim 16, wherein the pull wire extends from the proximal end of the elongate member to the first fixation member through at least a portion of the wall of the elongate member.

18. The catheter of claim 15, wherein the wall comprises:
an elongate core layer defining an exterior surface and an interior surface defining the longitudinally extending lumen;
an inner layer disposed on the interior surface of the elongate core layer; and
an outer layer disposed on the exterior surface of the elongate core layer, wherein the pull wire is disposed between the inner layer and the core layer, through the inner layer, or both.

* * * * *